United States Patent
Brugliera

(10) Patent No.: US 8,288,612 B2
(45) Date of Patent: Oct. 16, 2012

(54) GENETICALLY MODIFIED PLANTS WITH ALTERED INFLORESCENCE

(75) Inventor: Filippa Brugliera, Preston (AU)

(73) Assignee: Suntory Holdings Limited, Osaka-shi, Osaka (JP)

( * ) Notice: Subject to any disclaimer, the term of this patent is extended or adjusted under 35 U.S.C. 154(b) by 0 days.

(21) Appl. No.: 12/747,470

(22) PCT Filed: Nov. 14, 2008

(86) PCT No.: PCT/AU2008/001700
§ 371 (c)(1),
(2), (4) Date: Aug. 2, 2010

(87) PCT Pub. No.: WO2009/062259
PCT Pub. Date: May 22, 2009

(65) Prior Publication Data
US 2010/0293668 A1      Nov. 18, 2010

Related U.S. Application Data

(60) Provisional application No. 60/988,293, filed on Nov. 15, 2007.

(51) Int. Cl.
| C12N 15/82 | (2006.01) |
| C12N 5/10 | (2006.01) |
| C12N 15/29 | (2006.01) |
| A01H 5/00 | (2006.01) |
| A01H 1/02 | (2006.01) |

(52) U.S. Cl. ............ 800/282; 800/323.3; 800/260; 435/419; 435/468

(58) Field of Classification Search .......... None
See application file for complete search history.

(56) References Cited

FOREIGN PATENT DOCUMENTS

| EP | 1 652 916 | 5/2006 |
| WO | WO 94/03591 | 2/1994 |
| WO | WO 96/36716 | 11/1996 |
| WO | WO 2004/020637 | * 3/2004 |

OTHER PUBLICATIONS

Mol et al. Novel coloured flowers, 1999, Current Opinion in Biotechnology 10:198-201.*
Holton, et al. "Cloning and Expression of Cytochrome P450 Genes Controlling Flower Colour," *Nature*, vol. 366, No. 6452, pp. 276-279, 1993.
Tanaka, et al. "Flower Colour," *Flowering and Its Manipulation* (Book Series: *Annual Plant Reviews*), Blackwell Publishing, Chapter 9, pp. 201-239, Jan. 1, 2006.
Tanaka, Yoshikazu, "Flower Colour and Cytochromes P450," *Phytochemistry reviews*, vol. 5, Nos. 2-3, pp. 283-291, Oct. 31, 2006.
Tanaka, et al. Genetic Engineering in Floriculture, *Plant Cell, Tissue and Organ Culture*, vol. 80, No. 1, pp. 1-24, Jan. 1, 2005.
Supplementary European Search Report mailed Jul. 30, 2010, issued to European patent application EP 08 84 9461.
International Search Report dated Feb. 3, 2009, issued to international application No. PCT/AU2008/001700.

* cited by examiner

*Primary Examiner* — David T Fox
*Assistant Examiner* — Steven Bernacki
(74) *Attorney, Agent, or Firm* — Knobbe, Martens, Olson & Bear, LLP

(57) ABSTRACT

The present invention relates to genetically modified plants expressing altered inflorescence. More particularly, expression of at least two flavonoid 3'S' hydroxylases and at least one dihydroflavonol-4-reductase is achieved, leading to the production of dephinidin pigments and altered color phenotypes.

9 Claims, 5 Drawing Sheets

SEQUENCE LISTING

```
<160> NUMBER OF SEQ ID NOS: 10

<210> SEQ ID NO 1
<211> LENGTH: 1648
<212> TYPE: DNA
<213> ORGANISM: artificial
<220> FEATURE:
<223> OTHER INFORMATION: BPF3'5'H#18.nt

<400> SEQUENCE: 1
agccaatatg gcaattccag tcactgacct tgctgtcgcg gttatccttt tcttgatcac      60
tcgcttccta gttcgttctc ttttcaagaa accaaccgga ccgctcccgc cgggtccttc     120
aggctggccc ttggtgggcg cgctccctct cctaggcgcc atgcctcacg tcacactagc     180
caacctcgct aaaaaatacg gtccgatcat gtacctaaaa atgggcacgt gcgacatggt     240
ggtcgcgtcc actcccgact cggctcgagc cttcctcaaa acctagacc tcaacttctc     300
```

```
cgaccgcccg cccaacgccg gcgccaccca tttggcgtac ggcgcgcagg acttggtctt    360
cgcgaagtac ggtccaaggt ggaagaccct aagaaaattg agcaacctcc acatgctagg    420
cgggaaggcg ctggacgatt gggctcacgt gagggctaac gagctaggcc acatgcttaa    480
cgccatgtgc gaggcgagcc ggtgcggaga gcccgtggtg ctggccgaga tgctcacgta    540
cgccatggcc aacatgatcg gtcaagtgat actgagtcgg cgcgtgttcg tcaccaaagg    600
gacagagtcg aacgagttca agatatggt ggtcgagttg atgacttccg cggggtattt     660
caacattggt gacttcatac cgtcgattgc ttggatggat ttgcaaggga tcgagcgagg    720
gatgaagaaa ttgcacacga aattcgatgt tttgttgacg aagatgatga aggagcacag    780
agcgacgagt catgagcgcg aagggaaatc ggatttcctc gacgtcctct tggaagaatg    840
cgagaataca aatggcgaga agcttaatgt taccaacgtc aaagctgtcc tcttgaactt    900
attcacggcg ggtacggaca catcttcaag cataatcgaa tgggcgttaa ccgaaatgat    960
gaagaatccg acgatcttaa aaagacccca agaagagatg gatcgagtca tcggtcgcga   1020
tcggagattg ctcgaatccg acgtttcgaa actcccgtat ttacaagcca tagcgaaaga   1080
aacatatcgt aaacacccat cgacacctct aaacctgccg aggattgcga tccaagcatg   1140
tgaagttgat ggctactaca tccccaaaga cacgaggctt agcgtcaaca tttgggcgat   1200
cggtcgggac ccaagtgttt gggagaatcc atcggagttc tcgcctgaaa gattcttgtc   1260
tgaggagaat gggaagatca gtccaggcgg gaatgatttt gagctgattc cgtttggagc   1320
agggaggaga atttgtgctg gacaaggat gggaatggtc cttgtaagtt atattttggg    1380
cactttggtc cattcttttg attggaaatt accaaatggg gtcagtgaga ttaacatgga   1440
tgagagtttt gggcttgcgt tgcaaaaggc cgtgcctctc tcggctacgg tcagtccacg   1500
attggcccca agcgcgtacg ttatatgagc tgatgggctg ggcctgagcc caaacatatt   1560
gggtgtgttt tatctgtaat ttttaatatt ataaagttcg taattttgta tttatggtta   1620
attatgagtt aaaaaaaaaa aaaaaaaa                                      1648
```

<210> SEQ ID NO 2  
<211> LENGTH: 506  
<212> TYPE: PRT  
<213> ORGANISM: artificial  
<220> FEATURE:  
<223> OTHER INFORMATION: BPF3'5'H#18.aa

<400> SEQUENCE: 2

```
Met Ala Ile Pro Val Thr Asp Leu Ala Val Ala Val Ile Leu Phe Leu
1               5                   10                  15

Ile Thr Arg Phe Leu Val Arg Ser Leu Phe Lys Lys Pro Thr Gly Pro
            20                  25                  30

Leu Pro Pro Gly Pro Ser Gly Trp Pro Leu Val Gly Ala Leu Pro Leu
        35                  40                  45

Leu Gly Ala Met Pro His Val Thr Leu Ala Asn Leu Ala Lys Lys Tyr
    50                  55                  60

Gly Pro Ile Met Tyr Leu Lys Met Gly Thr Cys Asp Met Val Val Ala
65                  70                  75                  80

Ser Thr Pro Asp Ser Ala Arg Ala Phe Leu Lys Thr Leu Asp Leu Asn
                85                  90                  95

Phe Ser Asp Arg Pro Pro Asn Ala Gly Ala Thr His Leu Ala Tyr Gly
            100                 105                 110

Ala Gln Asp Leu Val Phe Ala Lys Tyr Gly Pro Arg Trp Lys Thr Leu
        115                 120                 125
```

Arg Lys Leu Ser Asn Leu His Met Leu Gly Gly Lys Ala Leu Asp Asp
            130                 135                 140

Trp Ala His Val Arg Ala Asn Glu Leu Gly His Met Leu Asn Ala Met
145                 150                 155                 160

Cys Glu Ala Ser Arg Cys Gly Glu Pro Val Val Leu Ala Glu Met Leu
                165                 170                 175

Thr Tyr Ala Met Ala Asn Met Ile Gly Gln Val Ile Leu Ser Arg Arg
            180                 185                 190

Val Phe Val Thr Lys Gly Thr Glu Ser Asn Glu Phe Lys Asp Met Val
        195                 200                 205

Val Glu Leu Met Thr Ser Ala Gly Tyr Phe Asn Ile Gly Asp Phe Ile
210                 215                 220

Pro Ser Ile Ala Trp Met Asp Leu Gln Gly Ile Glu Arg Gly Met Lys
225                 230                 235                 240

Lys Leu His Thr Lys Phe Asp Val Leu Leu Thr Lys Met Met Lys Glu
                245                 250                 255

His Arg Ala Thr Ser His Glu Arg Glu Gly Lys Ser Asp Phe Leu Asp
            260                 265                 270

Val Leu Leu Glu Glu Cys Glu Asn Thr Asn Gly Glu Lys Leu Asn Val
        275                 280                 285

Thr Asn Val Lys Ala Val Leu Leu Asn Leu Phe Thr Ala Gly Thr Asp
290                 295                 300

Thr Ser Ser Ser Ile Ile Glu Trp Ala Leu Thr Glu Met Met Lys Asn
305                 310                 315                 320

Pro Thr Ile Leu Lys Lys Thr Gln Glu Glu Met Asp Arg Val Ile Gly
                325                 330                 335

Arg Asp Arg Arg Leu Leu Glu Ser Asp Val Ser Lys Leu Pro Tyr Leu
            340                 345                 350

Gln Ala Ile Ala Lys Glu Thr Tyr Arg Lys His Pro Ser Thr Pro Leu
        355                 360                 365

Asn Leu Pro Arg Ile Ala Ile Gln Ala Cys Glu Val Asp Gly Tyr Tyr
370                 375                 380

Ile Pro Lys Asp Thr Arg Leu Ser Val Asn Ile Trp Ala Ile Gly Arg
385                 390                 395                 400

Asp Pro Ser Val Trp Glu Asn Pro Ser Glu Phe Ser Pro Glu Arg Phe
                405                 410                 415

Leu Ser Glu Glu Asn Gly Lys Ile Ser Pro Gly Gly Asn Asp Phe Glu
            420                 425                 430

Leu Ile Pro Phe Gly Ala Gly Arg Arg Ile Cys Ala Gly Thr Arg Met
        435                 440                 445

Gly Met Val Leu Val Ser Tyr Ile Leu Gly Thr Leu Val His Ser Phe
450                 455                 460

Asp Trp Lys Leu Pro Asn Gly Val Ser Glu Ile Asn Met Asp Glu Ser
465                 470                 475                 480

Phe Gly Leu Ala Leu Gln Lys Ala Val Pro Leu Ser Ala Thr Val Ser
                485                 490                 495

Pro Arg Leu Ala Pro Ser Ala Tyr Val Ile
            500                 505

<210> SEQ ID NO 3
<211> LENGTH: 1617
<212> TYPE: DNA
<213> ORGANISM: artificial
<220> FEATURE:
<223> OTHER INFORMATION: SalF3'5'H#47.nt

<400> SEQUENCE: 3

```
agatagtaag catggaagcc aagaaaata tgttgttgat tgctagggca cttgttgtag      60
catccttact ctacattttg atccgtatgt ttatctcaaa attgagcacc cccggccacc    120
ctctgccccc ggggccgagg ggcttttccag tggtgggctc ccttcccttg ctgggcgaca   180
tgccacatgt tgccctagca aaaatggcca aaactttatgg cccgatcatg tacttgaaaa   240
tgggcacagt cggcatggtc gtggcgtcca cgccagacgc ggcgcgggcg ttcctaaaaa    300
cccaggacgc taatttctct aaccggccgg tcaacgcggg tgccaccatc ctggcataca   360
atgcccagga catggtgttt gccccgtacg gccccaagtg gagattgctg aggaagctga   420
gcagtctcca catgctgggg agcaaggccc tggaggagtg ggccgacgtc cggacctcgg   480
aggtggggca catgctggcg gcgatgcacg aggccagccg cctggacgag gccgtggggt   540
tgccggagat gctggtgtac gcgacggcga acatgatcgg gaaggtgata ttgagccgga   600
gagttttcgt gacgaaaggg aaggagatga atgagttcaa ggaaatggtg gtggagctca   660
tgaccacagc tggctatttc aacattggtg atttcattcc atggcttgct tggatggatt   720
tgcagggat tgagagaggg atgaagaaac tgcacaagaa gtgggaccgc ttgatcggta    780
agatgctgga tgatcgattg aaatcaacct acaaacgcaa cgacaagcca gatcttcttg   840
attctctctt ggcaaatcat gatgatgaga gtaaggatga tgatgaggat tgcaagctca   900
ccaccaccaa tattaaagcc ctttactga atttatttac tgcagggaca gacacatcgt   960
cgagcataat agaatgggca ctagcggaga tgatcaagaa tccaagcatc caaaaaggg   1020
ctcaccaaga gatggacaga gtcatcggga gagagcggcg tttgctcgaa tccgacatcc   1080
caaatctgcc atacctcaaa gccatatgca agaggcata ccgaaaacac ccttccacgc   1140
cactaaaacct gcctcggatc tccacggatg catgcgtcgt cgatggctac cacatcccca   1200
agaacacgag gttgagcgtc aacatctggg ccataggccg agatcccgac gtttgggaga   1260
atccccttga cttcaaccct gacaggttta tgtcagggtt gcaggggatt gagcccggag   1320
ggaatcactt cgagctcatt ccctttgggg cggggcgcag gatctgcgcc ggcagcagaa   1380
tggggattgt aatagtggag tatttgctgg cgacactcgt gcactcttc gaatgggatt    1440
tgccagccgg ctcagcggag atggacatgg aggaggtgtt cgggctggcc ttgcagaaag   1500
ctgtaccact tgctgctagg ctcactccta ggttgccttc acattgctat gcacctcctt   1560
ctatttaatt tgcatatta tatatgttgt gttacattga aaaaaaaa aaaaaaa       1617
```

<210> SEQ ID NO 4
<211> LENGTH: 518
<212> TYPE: PRT
<213> ORGANISM: artificial
<220> FEATURE:
<223> OTHER INFORMATION: SalF3'5'H#47.aa

<400> SEQUENCE: 4

```
Met Glu Ala Gln Glu Asn Met Leu Leu Ile Ala Arg Ala Leu Val Val
1               5                  10                  15

Ala Ser Leu Leu Tyr Ile Leu Ile Arg Met Phe Ile Ser Lys Leu Ser
                20                  25                  30

Thr Pro Gly His Pro Leu Pro Pro Gly Pro Arg Gly Phe Pro Val Val
            35                  40                  45

Gly Ser Leu Pro Leu Leu Gly Asp Met Pro His Val Ala Leu Ala Lys
        50                  55                  60

Met Ala Lys Thr Tyr Gly Pro Ile Met Tyr Leu Lys Met Gly Thr Val
```

```
            65                  70                  75                  80
Gly Met Val Val Ala Ser Thr Pro Asp Ala Ala Arg Ala Phe Leu Lys
                    85                  90                  95

Thr Gln Asp Ala Asn Phe Ser Asn Arg Pro Val Asn Ala Gly Ala Thr
                100                 105                 110

Ile Leu Ala Tyr Asn Ala Gln Asp Met Val Phe Ala Pro Tyr Gly Pro
                115                 120                 125

Lys Trp Arg Leu Leu Arg Lys Leu Ser Ser Leu His Met Leu Gly Ser
            130                 135                 140

Lys Ala Leu Glu Glu Trp Ala Asp Val Arg Thr Ser Glu Val Gly His
145                 150                 155                 160

Met Leu Ala Ala Met His Glu Ala Ser Arg Leu Asp Glu Ala Val Gly
                165                 170                 175

Leu Pro Glu Met Leu Val Tyr Ala Thr Ala Asn Met Ile Gly Lys Val
                180                 185                 190

Ile Leu Ser Arg Arg Val Phe Val Thr Lys Gly Lys Glu Met Asn Glu
            195                 200                 205

Phe Lys Glu Met Val Val Glu Leu Met Thr Thr Ala Gly Tyr Phe Asn
210                 215                 220

Ile Gly Asp Phe Ile Pro Trp Leu Ala Trp Met Asp Leu Gln Gly Ile
225                 230                 235                 240

Glu Arg Gly Met Lys Lys Leu His Lys Lys Trp Asp Arg Leu Ile Gly
                245                 250                 255

Lys Met Leu Asp Asp Arg Leu Lys Ser Thr Tyr Lys Arg Asn Asp Lys
                260                 265                 270

Pro Asp Leu Leu Asp Ser Leu Leu Ala Asn His Asp Asp Glu Ser Lys
            275                 280                 285

Asp Asp Asp Glu Asp Cys Lys Leu Thr Thr Thr Asn Ile Lys Ala Leu
290                 295                 300

Leu Leu Asn Leu Phe Thr Ala Gly Thr Asp Thr Ser Ser Ser Ile Ile
305                 310                 315                 320

Glu Trp Ala Leu Ala Glu Met Ile Lys Asn Pro Ser Ile Gln Lys Arg
                325                 330                 335

Ala His Gln Glu Met Asp Arg Val Ile Gly Arg Glu Arg Arg Leu Leu
                340                 345                 350

Glu Ser Asp Ile Pro Asn Leu Pro Tyr Leu Lys Ala Ile Cys Lys Glu
            355                 360                 365

Ala Tyr Arg Lys His Pro Ser Thr Pro Leu Asn Leu Pro Arg Ile Ser
            370                 375                 380

Thr Asp Ala Cys Val Val Asp Gly Tyr His Ile Pro Lys Asn Thr Arg
385                 390                 395                 400

Leu Ser Val Asn Ile Trp Ala Ile Gly Arg Asp Pro Asp Val Trp Glu
                405                 410                 415

Asn Pro Leu Asp Phe Asn Pro Asp Arg Phe Met Ser Gly Leu Gln Gly
                420                 425                 430

Ile Glu Pro Gly Gly Asn His Phe Glu Leu Ile Pro Phe Gly Ala Gly
            435                 440                 445

Arg Arg Ile Cys Ala Gly Ser Arg Met Gly Ile Val Ile Val Glu Tyr
            450                 455                 460

Leu Leu Ala Thr Leu Val His Ser Phe Glu Trp Asp Leu Pro Ala Gly
465                 470                 475                 480

Ser Ala Glu Met Asp Met Glu Glu Val Phe Gly Leu Ala Leu Gln Lys
                485                 490                 495
```

Ala Val Pro Leu Ala Ala Arg Leu Thr Pro Arg Leu Pro Ser His Cys
            500                 505                 510

Tyr Ala Pro Pro Ser Ile
        515

<210> SEQ ID NO 5
<211> LENGTH: 4958
<212> TYPE: DNA
<213> ORGANISM: artificial
<220> FEATURE:
<223> OTHER INFORMATION: Pet gen DFR.nt

<400> SEQUENCE: 5

```
gatctggggt tgtcggcggt agaattggtc aaatcgatcc tcggtggaag agcaggcggc      60
gacatccttg agaagtgtgg agattctggt ggtacacgca cggcaccagt ggcgaggttt     120
aagccggcgc cagtgtatga agaggctgag cgccgacact gtggttaggg ggttttgggt     180
tgggtgtggt gggagtttgg gggggtcggg ttgtacgaga gcatgtgata ttgggggcag     240
ggggtgggag ttggttttgg gtgtgattgg tggattagag tttatatttg tgttagaaaa     300
aataatgtta tggcttgtaa attgagaaat attgctaatt ttatgtaata taggagtgta     360
atttgtatat atgcgtaaaa aatccaagaa acatggtgtt gcatcagggg gaaaagcgag     420
attcaagaag cttgataaga tagataatcc agaatatatt cattagagga gctggaatga     480
gaaggttaga taggaaaatg caaagtctta acttttaccc aatgtaaatg tagctatggt     540
agttatggta gttggtagaa gtagtagagt atcttggccc gagagtggaa atgtccacc     600 tcagatagat tgttgagctt tattgtttac ttggtaataa agttaattaa ttaccaaaaa     660
aaaaaaggaa gcatgtgatt atttagtgct tatcacttta ttgaatgtct atgccatgta     720
aattttcctt tatgttcata gcaagacaat attgatttaa tacagattga cccacctacg     780
tcgcaaatat actcaaattt aattttcaaa cttacaagta tatgataata agcttttta     840 agtagtttat ttgtgtaatt gttccataaa aaaaatttgg gcagacgtac ttgtgggatt     900
tgccataaaa aagagaaatg gaaatatttta aaaacctacg taatcgacac ccggcttttgg     960 agaaaattct ttagagaaat gtcgaaacct aacgaatgaa gagttactgg aaaatatgtc    1020
aaatatattt tgacaaattc aaattaaaag gaagatgaac tcaatcgttg cataaattat    1080
tagatttttt aatgaacttt aaacttgatt ccctaacctg ttgaacgtgt tagggctttt    1140
gacctgaatt tttaaactat taggactcct cttattgaag ggatgaaaaa gactcctaat    1200
tgaaatatat ctcctttata tgacttatcc tttacttaga ggagaagtaa tagacaacaa    1260
taaatagatg atcttcttct cacaatacac aacacaaatt ctacaatgta gtcttaggag    1320
aattttattt aggggagatt tttcttccca tattatgtag gccagttggc caaactactt    1380
tcaataacaa cccttttgat atgtgtcatt ttcatatttg attcattgtc attaatgttt    1440
gtgtgttagc ttccgcatgc atcatgttgt tccgatccca acaagtagta tcagagccat    1500
attcaactaa tggttcgatg agccaggttg ataaggttga agatatgttc aaggcggttt    1560
cagagctgca accaatgacg ataataaagt tatataaaaa ataggatggt aatgctacgt    1620
gtggagaaaa gttttttcaac catatattca acaataatgt tgctgctgca tctttaaaac    1680
aaaatacttt ttaacccatg ttttggctac ttttaaccaa tctcagtttt aactcatgct    1740
tattttaatg cttgggctcc cttttaatcc attcttgggc tcattttta cctgttgctg    1800 ggcttctttg aaccaaaata atattttaa acatgacaaa cagcagtttg aagaccatgt    1860
gaagaaggaa gatcaagatt cttttgtcca aaattcaggc caaggcggga attgttagtg    1920
```

```
tttttaccct gaattttaa cctattagga ctactcttat tgaagggatg aaaaagactc    1980
ctaattagaa tatatctcat ttatatgact tatccttaga ggagaagtaa tagacaacaa    2040
taaatagagg atcttcttct cacaacacac aacacaaatt ccacaatgta gtcttaggag    2100
aattttattt aggggagatt tttcttccca tattatgtag cccagttggc caaactactt    2160
tcaataacaa cccttttgat atgtgtcatt tttatatttg attcattgac attaatgttt    2220
gtgtgttagc ttccgcatgc accatgttgt ttcgatccca acggaaggga cacatggtaa    2280
cattcaatgc cagtttctca atttcgacca acatccaaaa gatgatattg catatatgga    2340
ttgaaaatat gtttcttcat cacggtacga ctcaatgatc tttctaaaat cggaaaattt    2400
ctaaggactg catggttcga aactcaaaaa tgataaatat atcccttat  cattctccac    2460
taaatattag gttgttcgaa cctataaatt acggctttcc acacatcacg tgttgcgtta    2520
caactaaacc aaaaccattg gaatcagtgg cggagccacc tttgggcaag ggaattcaat    2580
tgaaccctct tcaccgaaaa tttgtactgc attgatattt taaattttga acctcttatt    2640
gaaaatcctg tctccgtcct gcttggagca acaacacaac tctatatgca tatgaaagag    2700
tgggtcctaa gtaaccagat actacaccat ccccacagcc ccatttcctt ctctctcagc    2760
aaccagtcct atttagttaa tccaatgaag ttactcaacg ggccgttgag cacgtgctca    2820
ccatctaaca ttcccaatcc ttagacaacc tacgtgcaag tactataaag acagatataa    2880
accaacacat aaataaagtt catcctgttg taatttaact actagtaagt ccactaaaat    2940
taacaaaatc ttaagtccga ctttccaact tccatatctg ataatggcaa gtgaagcagt    3000
tcatgcccct tcacctccgg tggcagtgcc gacagtttgc gtcactggag ctgctggatt    3060
tattggctct tggcttgtca tgagactcct tgaacgcggt tacaatgttc acgctactgt    3120
tcgtgatcct ggtatgtttt gttcgagag tttaacttct atgcattgct agcgtaaaag    3180
aactttgaaa gtggtatgcg cgtgaagaga agtatgtgac attgataaaa gtgtgcccct    3240
tgtatggcat gcacttacgt aaagatgcat gattttgtag agaacaagaa gaaggtgaaa    3300
catctgctgg aactgccaaa ggctgatacg aacttaacac tgtggaaagc ggacttgaca    3360
gtagaaggaa gctttgacga ggccattcaa ggctgtcaag gagtatttca tgtagcaaca    3420
cctatggatt tcgagtccaa agaccctgag gtacgatcaa actagaagca aatatacttg    3480
tggtcctttc tacatttctg gtctaaattc taacataact atgtaacatc gagatatgac    3540
agaatgaagt aatcaagcca acagtccggg gaatgctaag catcattgaa tcatgtgcta    3600
aagcaaacac agtgaagagg ctggttttca cttcatctgc tggaactctc gatgtgcaag    3660
agcaacaaaa acttttctat gaccagacca gctggagcga cttggacttc atatatgcta    3720
agaagatgac aggatgggtt tgtttggcta ttcttttcat ttcgtaatac actctagtaa    3780
caaaaacagc attctcattg atacttgtga attaatttca ttgcagatgt attttgcttc    3840
caagatactg gcagagaaag ccgcaatgga agaagctaaa aagaagaaca ttgatttcat    3900
tagcatcata ccaccactgg ttgttggtcc attcatcaca cctacatttc cccctagttt    3960
aatcactgcc ctttcactaa ttactggtat gctgtagtct taaatattct acgtaattaa    4020
attgcacaga tgatgtgcag ttcttcctct caccaaacac cccacaaatt atttcaatta    4080
acaatatttt tacagtcatg ggtttaatca gattggggta tgcagggaat gaagctcatt    4140
actgcatcat taaacaaggt caatatgtgc atttggatga tctttgtgag gctcacatat    4200
tcctgtatga gcaccccaag gcagatggaa gattcatttg ctcgtcccac catgctatca    4260
tctacgatgt ggctaagatg gtccgagaga atggccaga gtactatgtt cctactgagt    4320
```

```
aagcctctct cttctgtatt cccaagtata gtaggctcct tcattgagtg atggcttagt    4380
aactcactcg tgggtaaata acaggtttaa agggatcgat aaagacctgc cagtggtgtc    4440
tttttcatca agaagctga cagatatggg ttttcagttc aagtacactt tggaggatat     4500
gtataaaggg gccatcgata cttgtcgaca aaagcagctg cttcccttt ctaccccgaag    4560 tgctgaagac aatggacata accgagaagc cattgccatt tctgctcaaa actatgcaag    4620
tggcaaagag aatgcaccag ttgcaaatca tacagaaatg ttaagcaatg ttgaagtcta    4680
gaactgcaat cttacaagat aaagaaagct tgccaagcaa tatgtttgct actaagttct    4740
ttgtcatctg tttgagggtt tcaaaacta atcagtaaa tttttcgatg catatagaga      4800
agttcttgtc ttgctaaatt acgggcagct aaacaatagg atatcaagaa tcccgtgcta    4860 tattttcag gaaaataaaa tctataatca tttcagggaa tctggatact aatacaagga     4920
cgtattttcc aatttataag ctttgcaaaa gcaagatc                            4958
```

<210> SEQ ID NO 6
<211> LENGTH: 380
<212> TYPE: PRT
<213> ORGANISM: artificial
<220> FEATURE:
<223> OTHER INFORMATION: Pet gen DFR.aa

<400> SEQUENCE: 6

```
Met Ala Ser Glu Ala Val His Ala Pro Ser Pro Val Ala Val Pro
1               5                   10                  15

Thr Val Cys Val Thr Gly Ala Ala Gly Phe Ile Gly Ser Trp Leu Val
            20                  25                  30

Met Arg Leu Leu Glu Arg Gly Tyr Asn Val His Ala Thr Val Arg Asp
        35                  40                  45

Pro Glu Asn Lys Lys Val Lys His Leu Leu Glu Leu Pro Lys Ala
    50                  55                  60

Asp Thr Asn Leu Thr Leu Trp Lys Ala Asp Leu Thr Val Glu Gly Ser
65                  70                  75                  80

Phe Asp Glu Ala Ile Gln Gly Cys Gln Gly Val Phe His Val Ala Thr
                85                  90                  95

Pro Met Asp Phe Glu Ser Lys Asp Pro Glu Asn Glu Val Ile Lys Pro
            100                 105                 110

Thr Val Arg Gly Met Leu Ser Ile Ile Glu Ser Cys Ala Lys Ala Asn
        115                 120                 125

Thr Val Lys Arg Leu Val Phe Thr Ser Ser Ala Gly Thr Leu Asp Val
    130                 135                 140

Gln Glu Gln Gln Lys Leu Phe Tyr Asp Gln Thr Ser Trp Ser Asp Leu
145                 150                 155                 160

Asp Phe Ile Tyr Ala Lys Lys Met Thr Gly Trp Met Tyr Phe Val Ser
                165                 170                 175

Lys Ile Leu Ala Glu Lys Ser Ala Met Glu Gly Thr Lys Lys Lys Asn
            180                 185                 190

Ile Asp Phe Ile Ser Ile Ile Pro Pro Leu Val Val Gly Pro Phe Ile
        195                 200                 205

Thr Pro Thr Phe Pro Pro Ser Leu Ile Thr Ala Leu Ser Leu Ile Thr
    210                 215                 220

Gly Asn Glu Ala His Tyr Cys Ile Ile Lys Gln Gly Gln Tyr Val His
225                 230                 235                 240

Leu Asp Asp Leu Cys Glu Ala His Ile Phe Leu Tyr Glu His Pro Lys
                245                 250                 255
```

```
Ala Asp Gly Arg Phe Ile Cys Ser Ser His His Ala Ile Ile Tyr Asp
                260                 265                 270

Val Ala Lys Met Val Arg Glu Lys Trp Pro Glu Tyr Tyr Val Pro Thr
            275                 280                 285

Glu Phe Lys Gly Ile Asp Lys Asp Leu Pro Val Val Ser Phe Ser Ser
        290                 295                 300

Lys Lys Leu Thr Asp Met Gly Phe Gln Phe Lys Tyr Thr Leu Glu Asp
305                 310                 315                 320

Met Tyr Lys Gly Ala Ile Glu Thr Cys Arg Gln Lys Gln Leu Leu Pro
                325                 330                 335

Phe Ser Thr Arg Ser Ala Ala Asp Asn Gly His Asn Arg Glu Ala Ile
            340                 345                 350

Ala Ile Ser Ala Gln Asn Tyr Ala Ser Gly Lys Glu Asn Ala Pro Val
        355                 360                 365

Ala Asn His Thr Glu Met Leu Thr Asn Val Glu Val
370                 375                 380
```

```
<210> SEQ ID NO 7
<211> LENGTH: 2544
<212> TYPE: DNA
<213> ORGANISM: artificial
<220> FEATURE:
<223> OTHER INFORMATION: carnANS 5'

<400> SEQUENCE: 7
```

| | | | | | |
|---|---|---|---|---|---|
| actcgaaatg | atactgtgag | tctgcgatag | gctcgttttg | aggcggaaat | tatgatttta | 60 |
| cgacgtgatc | aattgagcat | gacttaaatt | tgcgtcttct | cagtcgtcgt | tgcattgcaa | 120 |
| ttttagtat | tttcaggtgc | tctgaaagtg | tttagtacat | cgttttaaa | atggatatct | 180 |
| ttttgttctg | gtcgacttac | tcttcgcttt | ttaatgcaga | cgtgcccgtt | attgctacgt | 240 |
| gtattcacaa | aggtatgacc | gtgttctgta | gcgtctaatg | ataatatatg | aagtcgaggt | 300 |
| tgcatttgta | ctagtccgat | aataattagt | atcgttttca | tactgatact | agatcggagg | 360 |
| tcaccatacc | cgtgaagatt | tttctgtgag | aggaaaagaa | cccaaggacg | aggttcaaat | 420 |
| ctacacatgg | aaagacgcca | cgcttcgtga | gttaactgac | cttgtatgtc | gccatcgctt | 480 |
| agcgtagcgc | tgaacatcgt | tttcaccctg | ctccatccat | caaccattta | ttggtcttat | 540 |
| acatgtgtga | ttgcgttgtt | cttacattta | ggtgaaagac | gttctccag | ctgctaggag | 600 |
| tcgagatgcg | aaattgtcgt | ttgcgactgt | ataccttgat | agaaatggat | gcatgcaagt | 660 |
| aaagaaggta | tcttctaatt | catctttcgt | agagacatag | cgtgaatttg | acggggtct | 720 |
| ttggtttgag | aaagataaca | gctttacgta | ttttttgtaga | tgggtgaaac | cttttcaaat | 780 |
| ccgtataagc | gtaaagacga | caactgggct | tagggggaca | cattctttca | ggtataattg | 840 |
| atgcgactaa | caatagtctc | cactgatcat | attctactct | tctacgttcg | atactgactg | 900 |
| tttctggtta | tttggtagac | aggagattat | ttggacgtag | caattcagta | gcgtagagat | 960 |
| gtttccacac | gtgttatcgt | aaaagaagca | agataagcct | aatgcctagg | gtggtggtat | 1020 |
| gacttccgtt | gctatcgat | cgtgcttgta | agtaatttcc | gtcttatctt | ttcctgttat | 1080 |
| ataaagttaa | tcttctctag | gactttcatg | aaccttgttt | gtgtatttat | ttctcgatca | 1140 |
| acatgataga | gctagttttt | aagcaacgta | tactagtagt | ctattggaag | ttaagacacg | 1200 |
| gttcttaaaa | aggtacgatc | caagtgaagc | atgttagata | tgacactttc | ttctagggac | 1260 |
| gactctcgta | tgccacccga | cttttttcaat | tttttttgtg | aatgttagat | gtgtgtatat | 1320 |
| aatgcatccg | aaagatgtct | caacgaacaa | atgagccacc | tacttcgatc | actcgctatc | 1380 |

-continued

```
aatgttatta atgccttgtt gattttaata gttgatcaat aatagtaaaa tctattcaag     1440
ggtatagtct cccgttcaca ctcatcgggg ttacactagc gagctccatt aatcggtgcc     1500
ttaatcgaga cgctaagaac tataccatga cctagtcagc gccatgggac tgatgtaggc     1560
cacacaatct cgatgatccg aaaacgctag agttcaagac ctagttcgag accatggtca     1620
cggtttcaac cgcgatatct caacaatgca atttttttcg agactagaca gacgaataag     1680
tcttgtgtac gatgggtagc tagtgaatta aaggtaatca ctttactcgt gttcacaaga     1740
agaccattca tatgaacatt tcgtgttctc agacgagctc ctttcgctag tttggtaaac     1800
ttgtttggtg ttacctggct tatcatagcc cactcaattt ggcgaaaaca taacaattgt     1860
ttcacatgcg aaggtctaca cacccatact cgtgataaaa acggttgcat ttattattat     1920
tgcctttcga gcaatttacg ttgtttgaag tttgtgtaaa aacaaaatcg atctataatt     1980
actgactgga acgtaatat caaaactgtt aggacctgtt cttttcggct tataagagct      2040
gaacttataa aagctgtact tataggagct gagctgaact gaacttataa gagttgaact     2100
gaacttataa gggctgaaat taagctgtaa agaacaggtt cttatttcgc ctgatttgaa     2160
tccgactaaa gttggatgaa gatagaggcg agaaacgctc cccttccac agtttgactc      2220 tactcgaatc cgaccaaaat tggatgtaaa ttagaagtga gcattcctca tgccaaccac     2280
cgttcttggt cgtgaaaaca tgatttgtta gtctgctgta tacttcccaa acccgtgata     2340
atctgccaca cttccaacac ttaattgatt tttatcaaaa ttcctacagt ttttggttt      2400 tactcctaaa ctatgctgtc ttttttacaag ttgttcacacc tttgtcaaca actttatgct  2460
ttattatatt tcttatataa agaccatata acttccctac actaatgcca caacacttaa    2520
aagcatacaa cacaaacctc ataa                                            2544
```

<210> SEQ ID NO 8
<211> LENGTH: 822
<212> TYPE: DNA
<213> ORGANISM: artificial
<220> FEATURE:
<223> OTHER INFORMATION: carnANS 3'

<400> SEQUENCE: 8

```
actcactacg tgtttacgat tgtgtgtttg tcgtgtttgc ttaaatcgac catgtcctca      60
actttgagaa atcaatagtt gtacttttga gttattgtta tctcaataac gatattattg    120
cgttatacgg agtactgttt agaagacgat atgtaataaa tgaaatcgta gttgtctata   180
gcttcatgat tatcgttaca ctattattct tatacttcat cttttatttta gttaatctta   240 tcaaatactt cgtatattgg aaaatttcaa aaagttactt aaaaaataat aaaatacacc   300
gaatttcaga aaactcagga atattcaggc gtaataacat ccgttaatac cgaaaatatt    360
atgaaacgtg gcaaatgttg gacggtgtgc aatatgagac acaaaaaaac aattgtgaaa    420
aatctttggt cgtaacgaat tgcgtcctaa atcatcataa taatacaaat aaaaaaatgt    480 catttcatt aaatttcttc tcttctgtaa tcatagaatt ttattccaac ttcatcatct     540
aacttcaggt acatttctcc ttctctaact tattatcatt acttttatt gttttaaatt    600 atatttttta tgtctattaa acgatttaaa atgatcacag tttactctgt acttgtcgta    660
aataatgtgc tgtatgcata caacagtctt attggtttac gtgaactgtt agctgtggtt    720
gcatacaatt tagattgaac cgacagatat cgcctttact gtcggaggga gctgttacag    780
acttacgata ctgttcgtaa atggcaagct tgatatcgaa tt                       822
```

<210> SEQ ID NO 9

```
<211> LENGTH: 5645
<212> TYPE: DNA
<213> ORGANISM: artificial
<220> FEATURE:
<223> OTHER INFORMATION: Cin gF3'5'H.nt

<400> SEQUENCE: 9
cgatcgacat caccattgtg tcaatggtgt ttcggatatt tatgggacga cccaacaaaa      60
catgctttct aacacaaccc tccctcatcc cgagatttat acctggtcaa cggctcgacc     120
attgtccaag gcataagtta tggaaaagaa aaaataaaaa acatatagaa agtaaacttt     180
taaaacttgt gtaagcccaa attgtattac tcaagatcgg caggcgattt acgacctcag     240
ttacgtgttt aagcgtttga tatgtaaact tttacgagcg aaaaatgatc aagaaaattt     300
agtcatatga agttagaagt cattagattc tgtaatgtaa tgtatgtttc tggtatcaaa     360
agttattatc agtttgtgtt tctaaatcct aacagaatc aatatgcatt cgacttacag     420
tgattaagac gatcatagaa gggattatcg tcacaaaatt tagtcagata cttatgaact     480
gacaaaatcc tttacagaat caatatgcat tagacttaca gtgcaaacat atacgccgag     540
agctaaaagc gacggtgata agagtagaat cgtaatttca cagaatcagc agacttctta     600
taaagaaaac acaactagaa atcaagttca caaactactt catttactaa tctttgatgt     660
tcaacaagtc gttggcgagg gcatgggtac ttcggtaatt tcacacaact catgaatgtt     720
tttatgaaga aaacacttcc aagtataaac caagttctca aactaatatg ttcactaatc     780
aatgacgttc gagtaaatca cacctgaata caatgagcct agattttacc tggcaattcg     840
aattttcaaa ccattgaact aatcttttgc ataattctc ttgcaccaag atcatcgggt     900
gaacgagagg tccactcctg gtaatggcga agactaccag tgaaatctgt aaaaagcccg     960
tcaaggcgtc aactcccatt gtgtctatcc agtaattgta ttccatatat gggccttcac    1020
agaatttgaa atgcaagaac tggttttcat tgcgaaatgt gtaagggtgc agctgcaagt    1080
attagtaaaa gacgttcggt ttgacttttg aggtcaacac atagaaaaat tctactccaa    1140
ttttactcga agtaatgtga ttttcaggaa agattacaaa gaaactcgta acatatttaaa   1200
tatgggacaa tattagtatt aagaacttac ccagattcaa atcagtttga aaatttgaaa    1260
gttatatata aagataaaat ttgacctctc aaggtcaaac agagaaatcc aactccgttt    1320
atacacaacc ttaacgaaat tttaagaaaa tatcaacgat taccaaaaca gttctaacat    1380
gttaacacgt ggaaacgatt cgtctcttga gactaagtaa attatattta cattaatgtg    1440
tgattctgaa aaaggtcgt caaaatatct attaaatcta atgtacctgt agattatggg    1500
cgtgagctcg ggttttgaga ttgggaggcg tttgaatgta gttatctttc acaggaacaa    1560
cagtgtcttt ccatggacca ataccgacaa catattcttt gatatatttg aagtaacgat    1620
ctgaagtgat ttctgcatac gtctgcaaat gaaaagaaa tcagattata aacatccatt     1680
gcaaactatc cttgcatcgt gtttggatgt tcgttttaag cgagtatttt atggaatagg    1740
gagaatcaga caattagttg taataaaaca tgatctttaa ttgtgctact agtttaagtt    1800
ataatgataa tagaaaacat ttagtcttcg gaaaattata taaattacca aaaatgggtt    1860
taactgtttc aaaccaaaag tggcaagatg tcaggtcgga tggattgggt aacgggtcaa    1920
aatgggttgg actgaaacat gttcaaacat agcgcgtagg ccgtagagat tacaaaaatt    1980
ctccgttcca aataaggtta acagatatga ctatgctgac tttttaagtg tcaaatgcga    2040
ttctcttttc cggtatgcat aaaaaactga cgacggacat tacactatat aaaaatttag    2100
aaggttataa taaccaaga aaatataatt gtattaaatt gtgtgagtta tatgaattac      2160
```

```
atagaacctt ttatatatgg ttgaattacc ttgctgaaca agaaacctaa acctattaga    2220
aatgtctcaa aaatcctaag cttcaggaat accttcccgg ccttagcgac gaggaagata    2280
tgctagagtg tatgtgtgac tcgttaaaat catgaactag aacaaaggga aggaacaat     2340 gttacaatct caatgattag ataggatata actcgataac aaacctaacc agcagagtta    2400
gatcaagtgg taagtctttg cctttgaaga cataggtcga gggttcgatc ctcactccat    2460
gtggtcggag gtttattggt gaatgcatgc ttagctaccg ttcaaagtaa ctttattggt    2520
gaatgcatgc ttagctaccg ttcaaaatct tcaaaaggg taattatgtc taatatgcca     2580
tctaagttct aaccaaccct tcaaatgttc attcctataa ttactaacca attcttacgt    2640
tgtcaagtaa ataaaatgag cattctaacc ctaatctgca ccttcatcac tggtttgatg    2700
ttctatgggt tggttaattt gcttagccgt cgcgctagcc gtcttcctcc aggtccaacc    2760
ccatggccaa tcatcggcaa cctaatgcac cttggtaaac ttccacatca ctcgctggcg    2820
gacttggcga aaaagtatgg tccgttgata catgtccgac tagggtccgt tgatgttgtg    2880
gtggcctcgt ctgcgtccgt tgctgggcag ttttttaaagg tgcatgatgc gaattttgcc    2940
aacaggccac caaattctgg agctaaacat atggcgtata attatcatga tatggtgttt    3000
gcgccgtatg gtccaaggtg gcgaatgctt cgaaagatgt gctccatgca tctgttttct    3060
gccaaagcac tcactgattt tcgtcaagtt cgacaggttt tgtactttca ctttcgtcat    3120
atatataggg agattagtac gagaacgaac acttttaaaa tcacttttta ataatcaaaa    3180 tatcttttt tttttaaaca aaatcatgga atcttattca ataacttttt ctaaccttct     3240 aaatttttt taattttttta atttttttt tacttacagt gattaagata atcacataaa     3300
atatatagat aatcacatga aattttttgt gattatttag ttcaaataca ttattatcga    3360
tatatttttt gtgattatct taaccaccgt aaaaaaaatt caaaaataaa ataaaatctg    3420
agaaggttaa aaaagttata taaataagat tttccgattt tgttttcaac aataaaataa    3480
aatttcagaa cgtaataaaa attgatttt tgttaacgag agtttgtaac aatagacggt      3540
caacggaaaa tgtgtattat ctggtggtat caccatcgga ttatgccaag catgcataaa    3600
aaaacaaaat cgtaactaca ggaggaggta acgatactca cgcgcgtttt ggccaggact    3660
ggacaatcgg cagtgaaact agatcaacaa cttaacgtgt gcttcgcaaa cacattatcc    3720
cgaatgatgt tagacaggag agtatttgga gacggtgatc caaaggcgga cgactacaag    3780
gatatggtgg ttgagttgat gactttggcc ggacaattca acatcggtga ctacattcct    3840
tggcttgact tgcttgacct acaaggcatt gtcaaaagga tgaagaaagt tcattctcaa    3900
ttcgattcgt tccttgacac catcattgat gaacatacta ttggcacggg ccgtcatgtt    3960
gacatgttaa gcacaatgat ttcactcaaa gataatgccg atggagaggg agggaagctt    4020
tcgttcatcg agatcaaagc tcttctactg gtgcgcgtaa tacatagtag tcaactttt     4080 tttttttctg gtaatgactc tttgagcagg taaaatgtcc ccaacaggaa tcaaacttgg    4140
tacctatcat ttttgggaaa aatttaaaa gtactagctt tttcaaaaag attatgaaaa      4200
gtatctgttt ttctggacga ttgttaaatc taccccaaac gcatgtctta tatgcgttcc    4260
cttaatcaaa cgttgagggt gcgcatatgg tacatgcata ccctccaaag gagttcccat    4320
gcacgttgag ggtgcacata tacacatgcg caccctcttc gtggtttgcc accaaggcaa    4380
atcctggagg acagtcaacc tttttgatat aagttcagat ctaactctag gctaatactg    4440
ttgatgtttc agaacttgtt ctcagcggga acggacacgt catctagtac cgtggaatgg    4500
ggaatagcgg aactcattcg ccacccacag ctaatgaaac aagcgcaaga agaaatggac    4560
```

-continued

```
attgtagttg gaaaaaaccg gcttgtaaca gaaatggaca taagccaact aacattcctt    4620
caagccattg tgaaagaaac gtttaggcta caccccgcga cgccactttc cctgccaagg    4680
attgcatcag aaagctgtga ggtcaagggg tatcatgttc ctaagggatc gatactcttt    4740
gttaacgtgt gggccattgc tcgacaatca gaattgtgga ccgacccact tgaatttcgg    4800
cctggtcgtt tcctaatccc aggagaaaaa cctaatgttg aagtgaagcc aaatgatttc    4860
gaaattgtac cattcggggg aggacgaagg atttgtgcag gtatgagcct cggattgaga    4920
atggtcaatt tgcttattgc aacattggtt caagcctttg attgggaatt ggctaatggg    4980
ttagagccag aaaagcttaa catggaagaa gtgtttggga ttagccttca aagggttcaa    5040
cccttgttgg tgcacccgag gccaaggtta gcccgtcacg tatacggaac gggttaagga    5100
aataaactgt ctgtttgtaa gatgaatctg tttgaattta tgtattaaat agttatgcta    5160
agaactattt ttacaaataa agtatattg gtttgattgt tctcgcttag cctttgctaa    5220
atcttagata gatgagttgt ataacacatc atcattaact cacatcacgt ggtaacgatt    5280
tgtttttgag ttaaaatttt taaagaaagg aaagaaagag aaagtaaata taaaaaaatt    5340
tgtgttcccg agaagttttt tacgaaggaa gaggggagaa agagagagaa ttttagagaa    5400
attttgagta ttttacaaca aaaatcatcc tctcattttt gggatgattt ggaggatctt    5460
ttttctttct tttccttcgt ccacttcacc tcccttttctt tccaaaaaaa tctcggaaac    5520
atagcgtaat gataaacaaa aaccaataaa aatgagcagg agcaaaccct agaaggacga    5580
aatcttgaaa atttattcta agatttttaa aaaaaacttg gcagttggaa agggcggcgg    5640
atatc                                                                 5645
```

<210> SEQ ID NO 10
<211> LENGTH: 504
<212> TYPE: PRT
<213> ORGANISM: artificial
<220> FEATURE:
<223> OTHER INFORMATION: Cin gF3'5'H.aa

<400> SEQUENCE: 10

```
Met Ser Ile Leu Thr Leu Ile Cys Thr Phe Ile Thr Gly Leu Met Phe
1               5                   10                  15

Tyr Gly Leu Val Asn Leu Leu Ser Arg Arg Ala Ser Arg Leu Pro Pro
            20                  25                  30

Gly Pro Thr Pro Trp Pro Ile Ile Gly Asn Leu Met His Leu Gly Lys
        35                  40                  45

Leu Pro His His Ser Leu Ala Asp Leu Ala Lys Lys Tyr Gly Pro Leu
    50                  55                  60

Ile His Val Arg Leu Gly Ser Val Asp Val Val Ala Ser Ser Ala
65                  70                  75                  80

Ser Val Ala Gly Gln Phe Leu Lys Val His Asp Ala Asn Phe Ala Asn
                85                  90                  95

Arg Pro Pro Asn Ser Gly Ala Lys His Met Ala Tyr Asn Tyr His Asp
            100                 105                 110

Met Val Phe Ala Pro Tyr Gly Pro Arg Trp Arg Met Leu Arg Lys Met
        115                 120                 125

Cys Ser Met His Leu Phe Ser Ala Lys Ala Leu Thr Asp Phe Arg Gln
    130                 135                 140

Val Arg Gln Glu Glu Val Thr Ile Leu Thr Arg Val Leu Ala Arg Thr
145                 150                 155                 160

Gly Gln Ser Ala Val Lys Leu Asp Gln Gln Leu Asn Val Cys Phe Ala
                165                 170                 175
```

```
Asn Thr Leu Ser Arg Met Met Leu Asp Arg Arg Val Phe Gly Asp Gly
            180                 185                 190

Asp Pro Lys Ala Asp Asp Tyr Lys Asp Met Val Val Glu Leu Met Thr
            195                 200                 205

Leu Ala Gly Gln Phe Asn Ile Gly Asp Tyr Ile Pro Trp Leu Asp Leu
            210                 215                 220

Leu Asp Leu Gln Gly Ile Val Lys Arg Met Lys Lys Val His Ser Gln
225                 230                 235                 240

Phe Asp Ser Phe Leu Asp Thr Ile Ile Asp Glu His Thr Ile Gly Thr
                245                 250                 255

Gly Arg His Val Asp Met Leu Ser Thr Met Ile Ser Leu Lys Asp Asn
                260                 265                 270

Ala Asp Gly Glu Gly Gly Lys Leu Ser Phe Ile Glu Ile Lys Ala Leu
                275                 280                 285

Leu Leu Asn Leu Phe Ser Ala Gly Thr Asp Thr Ser Ser Ser Thr Val
        290                 295                 300

Glu Trp Gly Ile Ala Glu Leu Ile Arg His Pro Gln Leu Met Lys Gln
305                 310                 315                 320

Ala Gln Glu Glu Met Asp Ile Val Val Gly Lys Asn Arg Leu Val Thr
                325                 330                 335

Glu Met Asp Ile Ser Gln Leu Thr Phe Leu Gln Ala Ile Val Lys Glu
                340                 345                 350

Thr Phe Arg Leu His Pro Ala Thr Pro Leu Ser Leu Pro Arg Ile Ala
                355                 360                 365

Ser Glu Ser Cys Glu Val Lys Gly Tyr His Val Pro Lys Gly Ser Ile
        370                 375                 380

Leu Phe Val Asn Val Trp Ala Ile Ala Arg Gln Ser Glu Leu Trp Thr
385                 390                 395                 400

Asp Pro Leu Glu Phe Arg Pro Gly Arg Phe Leu Ile Pro Gly Glu Lys
                405                 410                 415

Pro Asn Val Glu Val Lys Pro Asn Asp Phe Glu Ile Val Pro Phe Gly
                420                 425                 430

Gly Gly Arg Arg Ile Cys Ala Gly Met Ser Leu Gly Leu Arg Met Val
                435                 440                 445

Asn Leu Leu Ile Ala Thr Leu Val Gln Ala Phe Asp Trp Glu Leu Ala
                450                 455                 460

Asn Gly Leu Glu Pro Glu Lys Leu Asn Met Glu Glu Val Phe Gly Ile
465                 470                 475                 480

Ser Leu Gln Arg Val Gln Pro Leu Leu Val His Pro Arg Pro Arg Leu
                485                 490                 495

Ala Arg His Val Tyr Gly Thr Gly
                500
```

GENETICALLY MODIFIED PLANTS WITH ALTERED INFLORESCENCE

This application is the U.S. National phase under 35 U.S.C. §371 of International Application PCT/AU2008/001700, filed Nov. 14, 2008. PCT/AU2008/001700 is associated with and claims priority from U.S. Provisional Patent Application No. 60/988,293, filed on 15 Nov. 2007, the entire contents of which, are incorporated herein into PCT/AU2008/001700 by reference.

FIELD

The present invention relates generally to the field of genetic modification of plants. More particularly, the present invention is directed to genetically modified plants expressing desired color phenotypes.

BACKGROUND

Bibliographic details of the publications referred to by the author in this specification are collected at the end of the description.

Reference to any prior art in this specification is not, and should not be taken as, an acknowledgment or any form of suggestion that this prior art forms part of the common general knowledge in any country.

The flower or ornamental or horticultural plant industry strives to develop new and different varieties of flowers and/or plants. An effective way to create such novel varieties is through the manipulation of flower color. Classical breeding techniques have been used with some success to produce a wide range of colors for almost all of the commercial varieties of flowers and/or plants available today. This approach has been limited, however, by the constraints of a particular species' gene pool and for this reason it is rare for a single species to have the full spectrum of colored varieties. For example, the development of novel colored varieties of plants or plant parts such as flowers, foliage, fruits and stems would offer a significant opportunity in both the cut flower, ornamental and horticultural markets. In the flower or ornamental or horticultural plant industry, the development of novel colored varieties of carnation is of particular interest. This includes not only different colored flowers but also anthers and styles.

Flower color is predominantly due to three types of pigment: flavonoids, carotenoids and betalains. Of the three, the flavonoids are the most common and contribute a range of colors from yellow to red to blue. The flavonoid molecules that make the major contribution to flower color are the anthocyanins, which are glycosylated derivatives of cyanidin and its methylated derivative peonidin, delphinidin and its methylated derivatives petunidin and malvidin and pelargonidin. Anthocyanins are localized in the vacuole of the epidermal cells of petals or the vacuole of the sub epidermal cells of leaves.

The flavonoid pigments are secondary metabolites of the phenylpropanoid pathway. The biosynthetic pathway for the flavonoid pigments (flavonoid pathway) is well established, (Holton and Cornish, *Plant Cell* 7:1071-1083, 1995; Mol et al, *Trends Plant Sci.* 3:212-217, 1998; Winkel-Shirley, *Plant Physiol.* 126:485-493, 2001a; and Winkel-Shirley, *Plant Physiol.* 127:1399-1404, 2001b, Tanaka and Mason, In *Plant Genetic Engineering*, Singh and Jaiwal (eds) SciTech Publishing Llc., USA, 1:361-385, 2003, Tanaka et al, *Plant Cell, Tissue and Organ Culture* 80:1-24, 2005, Tanaka and Brugliera, In *Flowering and Its Manipulation, Annual Plant Reviews* Ainsworth (ed), Blackwell Publishing, UK, 20:201-239, 2006) and is shown in FIG. 1. Three reactions and enzymes are involved in the conversion of phenylalanine to p-coumaroyl-CoA, one of the first key substrates in the flavonoid pathway. The enzymes are phenylalanine ammonialyase (PAL), cinnamate 4-hydroxylase (C4H) and 4-coumarate: CoA ligase (4CL). The first committed step in the pathway involves the condensation of three molecules of malonyl-CoA (provided by the action of acetyl CoA carboxylase (ACC) on acetyl CoA and $CO_2$) with one molecule of p-coumaroyl-CoA. This reaction is catalyzed by the enzyme chalcone synthase (CHS). The product of this reaction, 2',4,4',6', tetrahydroxy-chalcone, is normally rapidly isomerized by the enzyme chalcone flavanone isomerase (CHI) to produce naringenin. Naringenin is subsequently hydroxylated at the 3 position of the central ring by flavanone 3-hydroxylase (F3H) to produce dihydrokaempferol (DHK).

The pattern of hydroxylation of the B-ring of DHK plays a key role in determining petal color. The B-ring can be hydroxylated at either the 3', or both the 3' and 5' positions, to produce dihydroquercetin (DHQ) or dihydromyricetin (DHM), respectively. Two key enzymes involved in this part of the pathway are the flavonoid 3' hydroxylase (F3'H) and flavonoid 3',5' hydroxylase (F3'5'H), both members of the cytochrome P450 class of enzymes.

F3'H is a key enzyme in the flavonoid pathway leading to the cyanidin-based pigments which, in many plant species contribute to red and pink flower color.

The next step in the pathway, leading to the production of the colored anthocyanins from the dihydroflavonols (DHK, DHQ, DHM), involves dihydroflavonol-4-reductase (DFR) leading to the production of the leucoanthocyanidins. The leucoanthocyanidins are subsequently converted to the anthocyanidins, pelargonidin, cyanidin and delphinidin. These flavonoid molecules are unstable under normal physiological conditions and glycosylation at the 3-position, through the action of glycosyltransferases, stabilizes the anthocyanidin molecule thus allowing accumulation of the anthocyanins. In general, the glycosyltransferases transfer the sugar moieties from UDP sugars to the flavonoid molecules and show high specificities for the position of glycosylation and relatively low specificities for the acceptor substrates (Seitz and Hinderer, Anthocyanins. In: *Cell Culture and Somatic Cell Genetics of Plants*. Constabel and Vasil (eds.), Academic Press, New York, USA, 5:49-76, 1988). Anthocyanins can occur as 3-monosides, 3-biosides and 3-triosides as well as 3,5-diglycosides and 3,7-diglycosides associated with the sugars glucose, galactose, rhamnose, arabinose and xylose (Strack and Wray, In: *The Flavonoids—Advances in Research since* 1986. Harborne, J. B. (ed), Chapman and Hall, London, UK, 1-22, 1993).

Glycosyltransferases involved in the stabilization of the anthocyanidin molecule include UDP glucose: flavonoid 3-glucosyltransferase (3GT), which transfers a glucose moiety from UDP glucose to the 3-O-position of the anthocyanidin molecule to produce anthocyanidin 3-O-glucoside.

Many anthocyanidin glycosides exist in the form of acylated derivatives. The acyl groups that modify the anthocyanidin glycosides can be divided into two major classes based upon their structure. The aliphatic acyl groups include malonic acid or succinic acid and the aromatic class includes the hydroxy cinnamic acids such as p-coumaric acid, caffeic acid and ferulic acid and the benzoic acids such as p-hydroxybenzoic acid.

Methylation at the 3' and 5' positions of the B-ring of anthocyanidin glycosides can also occur. Methylation of cyanidin-based pigments leads to the production of peonidin. Methylation of the 3' position of delphinidin-based pigments results in the production of petunidin, whilst methylation of the 3' and 5' positions results in malvidin production. Methylation of malvidin can also occur at the 5-O and 7-O positions to produce capensinin (5-O-methyl malvidin) and 5,7-di-O-methyl malvidin.

In addition to the above modifications, pH of the vacuole or compartment where pigments are localized and co-pigmentation with other flavonoids such as flavonols and flavones can affect petal color. Flavonols and flavones can also be aromatically acylated (Brouillard and Dangles, In: *The Flavonoids—Advances in Research since 1986.* Harborne, J. B. (ed), Chapman and Hall, London, UK, 1-22, 1993).

Carnation flowers can produce two types of anthocyanidins, depending on their genotype—pelargonidin and cyanidin. In the absence of F3'H activity, pelargonidin is produced otherwise cyanidin is produced. Pelargonidin is usually accompanied by kaempferol, a colorless flavonol. Cyanidin pigments are usually accompanied by both kaempferol and quercetin. Both pelargonidin and kaempferol are derived from DHK; both cyanidin and quercetin are derived from DHQ (FIG. 1).

The substrate specificity shown by DFR regulates the anthocyanins that a plant accumulates. *Petunia* and cymbidium DFRs do not reduce DHK and thus they do not accumulate pelargonidin-based pigments (Forkmann and Ruhnau, *Z Naturforsch C.* 42c, 1146-1148, 1987, Johnson et al, *Plant Journal,* 19, 81-85, 1999). Many important floricultural species including iris, delphinium, cyclamen, gentian, cymbidium are presumed not to accumulate pelargonidin due to the substrate specificity of their endogenous DFRs (Tanaka and Brugliera, 2006, supra).

In carnation, the DFR enzyme is capable of metabolizing two dihydroflavonols to leucoanthocyanidins which are ultimately converted through to anthocyanins—pigments that are responsible for flower color. DHK is converted to leucopelargonidin, the precursor to pelargonidin-based pigments, giving rise to apricot to brick-red colored carnations. DHQ is converted to leucocyanidin, the precursor to cyanidin-based pigments, producing pink to red carnations. Carnation DFR is also capable of converting DHM to leucodelphinidin (Forkmann and Ruhnau, 1987 supra), the precursor to delphinidin-based pigments. However, wild-type or classically-derived carnation lines do not contain a F3'5'H enzyme and therefore do not synthesize DHM.

The petunia DFR enzyme has a different specificity to that of the carnation DFR. It is able to convert DHQ through to leucocyanidin, but it is not able to convert DHK to leucopelargonidin (Forkmann and Ruhnau, 1987 supra). It is also known that in petunia lines containing the F3'5'H enzyme, the petunia DFR enzyme can convert the DHM produced by this enzyme to leucodelphinidin which is further modified giving rise to delphinidin-based pigments which are predominantly responsible for blue colored flowers (see FIG. 1). Even though the petunia DFR is capable of converting both DHQ and DHM, it is able to convert DHM far more efficiently, thus favoring the production of delphinidin (Forkmann and Ruhnau 1987 supra).

The anthocyanins found in chrysanthemum are generally based on cyanidin. Delphinidin-based pigments are not present due to the lack of a F3'5'H activity and pelargonidin-based pigments are rarely found. It has been suggested that the absence of pelargonidin-based pigments in chrysanthemum is due to the presence of a F3'H activity rather than the DFR specificity. For example, when chrysanthemum petals were fed with a cytochrome P450 inhibitor, pelargonidin-based pigments were detected (Schwinn et al, *Phtochemistry,* 35:145-150, 1993).

Roses and gerberas generally accumulate anthocyanins based on cyanidin and/or pelargonidin. Delphinidin-based anthocyanins are generally not found in wild-type or classically derived rose or gerbera flowers primarily due to the absence of F3'5'H activity.

Nucleotide sequences encoding F3'5'Hs have been cloned (see International Patent Application No. PCT/AU92/00334 incorporated herein by reference and Holton et al, *Nature,* 366:276-279, 1993 and International Patent Application No. PCT/AU03/01111 incorporated herein by reference). These sequences were efficient in modulating 3',5' hydroxylation of flavonoids in petunia (see International Patent Application No. PCT/AU92/00334 and Holton et al, 1993 supra), tobacco (see International Patent Application No. PCT/AU92/00334), carnations (see International Patent Application No. PCT/AU96/00296 incorporated herein by reference) and roses (see International Patent Application No. PCT/AU03/01111).

Carnations are one of the most extensively grown cut flowers in the world.

There are thousands of current and past cut-flower varieties of cultivated carnation. These are divided into three general groups based on plant form, flower size and flower type. The three flower types are standards, sprays and midis. Most of the carnations sold fall into two main groups—the standards and the sprays. Standard carnations are intended for cultivation under conditions in which a single large flower is required per stem. Side shoots and buds are removed (a process called disbudding) to increase the size of the terminal flower. Sprays and/or miniatures are intended for cultivation to give a large number of smaller flowers per stem. Only the central flower is removed, allowing the laterals to form a 'fan' of stems.

Spray carnation varieties are popular in the floral trade, as the multiple flower buds on a single stem are well suited to various types of flower arrangements and provide bulk to bouquets used in the mass market segment of the industry.

Standard and spray cultivars dominate the carnation cut-flower industry, with approximately equal numbers sold of each type in the USA. In Japan, Spray-type varieties account for 70% of carnation flowers sold by volume, whilst in Europe spray-type carnations account for approximately 50% of carnation flowers traded through out the Dutch auctions. The Dutch auction trade is a good indication of consumption across Europe.

Whilst standard and midi-type carnations have been successfully manipulated genetically to introduce new colors (Tanaka and Brugliera, 2006, supra; see International Patent Application No. PCT/AU96/00296), this has not been applied to spray carnations. There is an absence of blue color in color-assortment in carnation, only recently filled through the introduction of genetically-modified standard-type carnation varieties. However, standard-type varieties can not be used for certain purposes, such as bouquets and flower arrangements where a large number of smaller carnation flowers are needed, such as hand-held arrangements, and small table settings.

One particular spray carnation which is particularly commercially popular is the Kortina Chanel line of carnations (*Dianthus caryophyllus* cv. Kortina Chanel). The variety has excellent growing characteristics and a moderate to good resistance to fungal pathogens such as *Fusarium*. There are a number of varieties which have been released as "sports" of Kortina Chanel. These include Kortina, Royal Red Kortina, Cerise Kortina and Dusty Kortina. However, before the advent of the present invention, purple/blue spray carnations were not available.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO). The SEQ ID NOs correspond numerically to the sequence identifiers <400>1 (SEQ ID NO:1), <400>2 (SEQ ID NO:2), etc.

A summary of sequence identifiers used throughout the subject specification is provided in Table 1.

The present invention provides genetically modified plants exhibiting altered inflorescence. More particularly, the present invention provides genetically modified carnations and even more particularly genetically modified carnation sprays exhibiting altered inflorescence. The altered inflorescence is a color in the range of red-purple to blue such as purple to blue color in the tissue or organelles including flowers, petals, anthers and styles. In one embodiment, the color is determined using the Royal Horticultural Society (RHS) color chart where colors are arranged in order of the fully saturated colors with the less saturated and less bright colors alongside. The color groups proceed through the observable spectrum and the colors referred to in this application are generally in the red-purple (RHSCC 58-74), purple (RHSCC 75-79), purple-violet (RHSCC 81-82), violet (RHSCC 83-88), violet-blue (89-98), blue (RHSCC 99-110) groups contained in Fan 2. Colors are selected from the range including 61A, 64A, 71A, 71C, 72A, 81A, 86A and 87A and colors in between or proximal thereto.

in selected tissue, the spray carnation comprising expressed genetic material encoding at least two F3'5'H enzymes and at least one DFR enzyme.

Yet another, aspect of the present invention is directed to a genetically modified Kortina Chanel spray carnation line or sport thereof exhibiting tissues of a purple to blue color, the carnation comprising expressed genetic sequences encoding at least two F3'5'H enzymes and at least one DFR enzyme.

Another aspect of the present invention is directed to a genetically modified chrysanthemum exhibiting tissues of a purple to blue color, the chrysanthemum comprising expressed genetic sequences encoding at least two F3'5'H enzymes and at least one DFR enzyme.

Still another aspect of the present invention is directed to a genetically modified rose exhibiting tissues of a purple to blue color, the rose comprising expressed genetic sequences encoding at least two F3'5'H enzymes and at least one DFR enzyme.

Even yet another aspect of the present invention is directed to a genetically modified gerbera exhibiting tissues of a purple to blue color, the gerbera comprising expressed genetic sequences encoding at least two F3'5'H enzymes and at least one DFR enzyme.

Yet another aspect of the present invention is directed to a genetically modified ornamental or horticultural plant exhibiting tissues of a purple to blue color, the ornamental or horticultural plant comprising expressed genetic sequences encoding at least two F3'5'H enzymes and at least one DFR enzyme.

TABLE 1

Summary of sequence identifiers

| SEQ ID NO: | NAME | SPECIES | TYPE OF SEQ | DESCRIPTION |
| --- | --- | --- | --- | --- |
| 1 | BPF3'5'H#18.nt | Viola sp | nucleotide | F3'5'H cDNA |
| 2 | BPF3'5'H#18.aa | Viola sp | amino acid | deduced F3'5'H amino acid sequence |
| 3 | SalF3'5'H#47.nt | Salvia sp. | nucleotide | F3'5'H cDNA |
| 4 | SalF3'5'H#47.aa | Salvia sp | amino acid | deduced F3'5'H amino acid sequence |
| 5 | Pet gen DFR.nt | Petunia sp | nucleotide | DFR genomic clone |
| 6 | Pet gen DFR.aa | Petunia sp | amino acid | deduced DFR amino acid sequence |
| 7 | CarnANS 5' | Dianthus caryophyllus | nucleotide | Carnation ANS promoter fragment |
| 8 | CarnANS 3' | Dianthus caryophyllus | nucleotide | Carnation ANS terminator fragment |
| 9 | Cin gF3'5'H.nt | Cineraria sp | nucleotide | F3'5'H genomic clone |
| 10 | Cin gF3'5'H.aa | Cineraria sp | amino acid | deduced F3'5'H amino acid sequence |

The modified plants and in particular genetically modified spray carnations comprise genetic sequences encoding at least two F3'5'H molecules and at least one DFR. Insofar as the present invention relates to carnations, the carnation sprays are conveniently in a Kortina Chanel genetic background including sports of Kortina Chanel such as Kortina, Royal Red Kortina, Cerise Kortina and Dusty Kortina. Other carnation cultivars included within the present invention are Cream Cinderella, Cinderella, Cerise Westpearl, Vega, Artisan and Rendezvous.

Hence, one aspect of the present invention is directed to a genetically modified plant exhibiting altered inflorescence in selected tissue, the plant comprising expressed genetic material encoding at least two F3'5'H enzymes and at least one DFR enzyme. The term "altered inflorescence" in this context means compared to the inflorescence of a plant (e.g. parent plant or plant of the same species) prior to genetic manipulation. The term "encoding" includes the expression of the genetic material to produce functional F3'5'H and DFR enzymes.

In a particular embodiment, the plant is a spray carnation.

Accordingly, another aspect of the present invention is directed to a spray carnation exhibiting altered inflorescence In a particular embodiment, the present invention provides a genetically modified spray carnation identified herein as Kortina Chanel (KC)/pCGP2442 and its progeny and sports.

Progeny, reproductive material, cut flowers, tissue culturable cells and regenerable cells from the genetically plants also form part of the present invention.

The present invention is also directed to the use of genetic sequences encoding at least two F3'5'H enzymes and at least one DFR enzyme in the manufacture of a genetically modified plant such as a spray carnation including a Kortina Chanel carnation or sports thereof exhibiting altered inflorescence including tissue having a purple to blue color.

The F3'5'H enzymes may be from any source and the two may come from the same or different plant species. Nucleotide sequences encoding F3'5'H enzymes from Viola sp and Salvia sp are particularly useful (see Table 1). Similarly, the nucleotide sequence encoding the DFR enzyme may come from any species such as but not limited to Petunia sp (e.g. see Table 1), iris, cyclamen, delphinium, gentian, Cymbidium. Suitable nucleotide sequences for F3'5'H from Viola sp and Salvia sp and a DFR from Petunia sp are set forth in Table 1.

BRIEF DESCRIPTION OF THE FIGURES

Some figures contain color representations or entities. Color photographs are available from the Patentee upon request or from an appropriate Patent Office. A fee may be imposed if obtained from a Patent Office.

DETAILED DESCRIPTION

Figure 1:
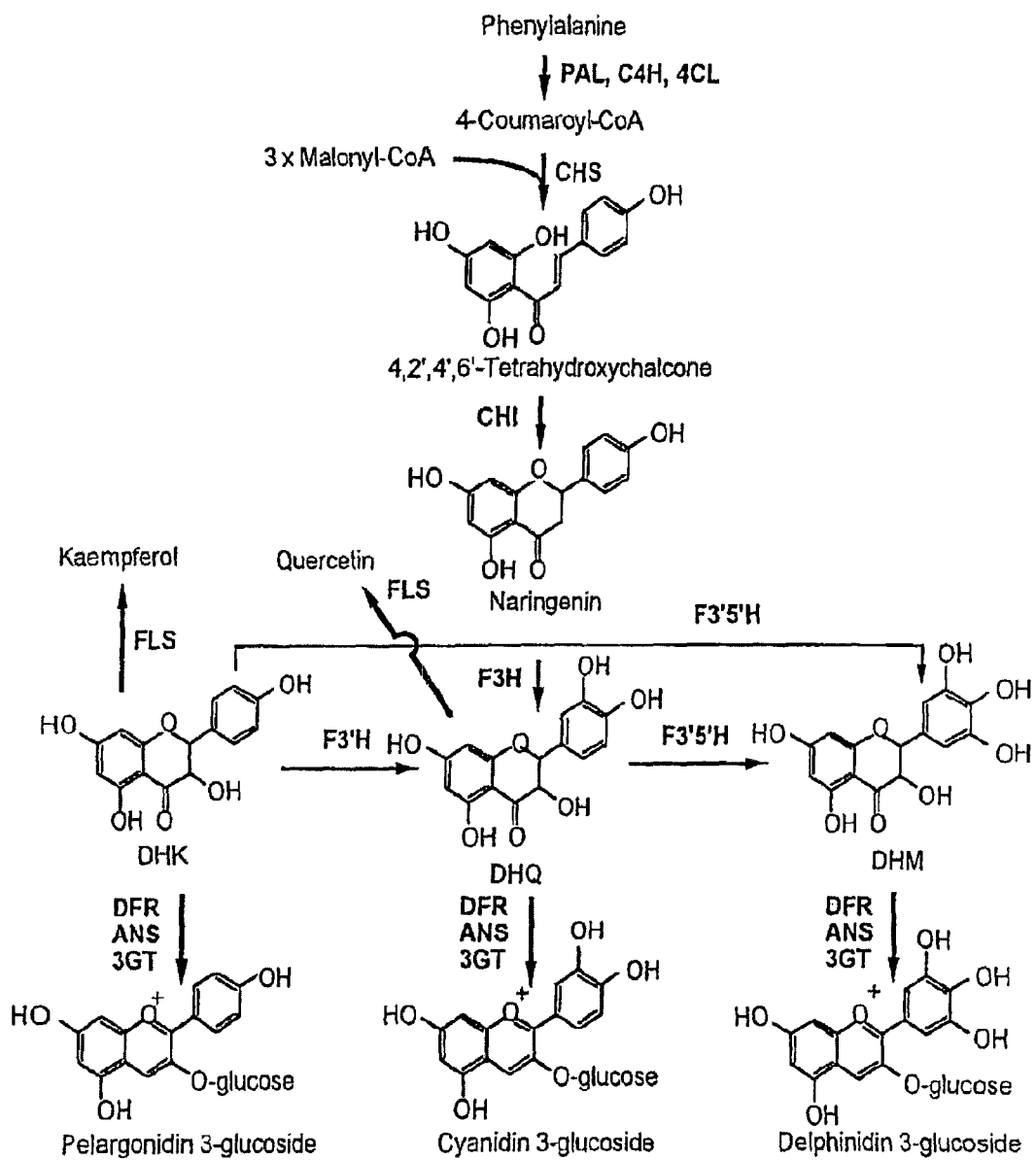
FIG. 1 is a schematic representation of the biosynthesis pathway for the flavonoid pigments showing production of the anthocyanidin 3-glucosides that occur in most plants that produce anthocyanins. Enzymes involved in the pathway have been indicated as follows: PAL=Phenylalanine ammonia-lyase; C4H=Cinnamate 4-hydroxylase; 4CL=4-coumarate:CoA ligase; CHS=Chalcone synthase; CHI=Chalcone flavanone isomerase; F3H=Flavanone 3-hydroxylase; DFR=Dihydroflavonol-4-reductase; ANS=Anthocyanidin synthase, 3GT=UDP-glucose: flavonoid 3-O-glucosyltransferase; Other abbreviations include: DHK=dihydrokaempferol, DHQ dihydroquercetin, DHM=dihydromyricetin.

As used in the subject specification, the singular forms "a", "an" and "the" include plural aspects unless the context clearly dictates otherwise. Thus, for example, reference to "a plant" includes a single plant, as well as two or more plants; reference to "an anther" includes a single anther as well as two or more anthers; reference to "the invention" includes a single aspect or multiple aspects of an invention; and so on.

The present invention contemplates genetically modified plants such as carnation plants and in particular spray carnations exhibiting altered inflorescence. The altered inflorescence may be in any tissue or organelle including flowers, petals, anthers and styles. Particular inflorescence contemplated herein includes a color in the range of red-purple to blue color such as a purple to blue color. The color determination is conveniently measured against the Royal Horticultural Society (RHS) color chart (RHSCC) and includes colors 81A, 86A, 87A and colors in between or proximal to either end of the above range. The term "inflorescence" is not to be narrowly construed and relates to any colored cells, tissues organelles or parts thereof, as well as flowers and petals.

Hence, one aspect of the present invention is directed to a genetically modified plant exhibiting altered inflorescence in selected tissue, the plant comprising expressed genetic material encoding at least two F3'5'H enzymes and at least one DFR enzyme.

In a particular embodiment, the plant is a carnation. Accordingly, another aspect of the present invention is directed to a spray carnation exhibiting altered inflorescence in selected tissue, the spray carnation comprising expressed genetic material encoding at least two F3'5'H enzymes and at least one DFR enzyme.

Whilst the present invention encompasses any spray carnation, a carnation of the Kortina Chanel line is particularly useful including sports thereof Useful sports of Kortina Chanel include Kortina, Royal Red Kortina, Cerise Kortina and Dusty Kortina.

Accordingly, another aspect of the present invention is directed to a genetically modified Kortina Chanel spray carnation line or sports thereof exhibiting tissues of a purple to blue color, the carnation comprising expressed genetic sequences encoding at least two F3'5'H enzymes and at least one DFR enzyme.

Even more particularly, the present invention provides a genetically modified Kortina Chanel (KC)/pCGP2442 (also referred to as KC/2442 or Kortina Chanel/2442) line exhibiting altered inflorescence, the line comprising an expressed genetic sequence encoding at least two F3'5'H enzymes and at least one DFR enzyme.

Examples of Kortina Chanel transgenic lines include 19890 and 19907.

Other genetically modified carnations contemplated herein include the spray carnations Cerise Westpearl, Vega and Artisan and the standard carnations Cream Cinderella, Cinderella and Rendezvous Other genetically modified plants contemplated herein include chrysanthemums, roses, gerberas, lisianthus, tulip, lily, geranium, petunia, iris, *Torenia, Begonia, Cyclamen, Nierembergia, Catharanthus, Pelargonium*, orchid, grape, apple, *Euphorbia* or *Fuchsia* and other ornamental or horticultural plants Another aspect of the present invention is directed to a genetically modified chrysanthemum exhibiting tissues of a purple to blue color, the chrysanthemum comprising expressed genetic sequences encoding at least two F3'5'H enzymes and at least one DFR enzyme.

Still another aspect of the present invention is directed to a genetically modified rose exhibiting tissues of a purple to blue color, the rose comprising expressed genetic sequences encoding at least two F3'5'H enzymes and at least one DFR enzyme.

Yet another aspect of the present invention is directed to a genetically modified gerbera exhibiting tissues of a purple to blue color, the gerbera comprising expressed genetic sequences encoding at least two F3'5'H enzymes and at least one DFR enzyme.

Yet another aspect of the present invention is directed to a genetically modified ornamental or horticultural plant exhibiting tissues of a purple to blue color, the ornamental or horticultural plant comprising expressed genetic sequences encoding at least two F3'5'H enzymes and at least one DFR enzyme.

The genetic sequence may be a single construct carrying the nucleotide sequences encoding the F3'5'H enzymes and the DFR enzyme or multiple genetic constructs may be employed. In addition, the genetic sequences may be integrated into the genome of a plant cell or it may be maintained as an extra-chromosomal artificial chromosome. Still furthermore, the generation of a spray carnation expressing two F3'5'H enzymes and at least one DFR enzyme may be generated by recombinant means alone or by a combination of conventional breeding and recombinant DNA manipulation. The genetic sequences are "expressed" in the sense of being operably linked to a promoter and other regulatory sequences resulting in transcription and translation to produce F3'5'H and DFR enzymes.

Hence, another aspect of the present invention contemplates a method for producing a genetically modified plant such as a spray carnation exhibiting altered inflorescence, the method comprising introducing into regenerable cells of a plant such as a spray carnation plant expressible genetic material encoding at least two F3'5'H enzymes and at least one DFR enzyme and regenerating a plant therefrom or obtaining progeny from the regenerated plant.

The plant may then undergo various generations of growth or cultivation. Hence, reference to a genetically modified spray carnation includes progeny thereof and sister lines thereof as well as sports thereof.

Another aspect of the present invention provides a method for producing a genetically modified plant such as a spray carnation line exhibiting altered inflorescence, the method comprising selecting a plant such as a spray carnation comprising expressible genetic material encoding one of at least two F3'5'H enzymes or at least one DFR enzyme and crossing this plant with another plant such as a spray carnation comprising genetic material encoding the other of at least two F3'5'H enzymes or at least one DFR enzyme and then selecting F1 or subsequent generation plants which express the genetic material.

Nucleotide sequences encoding F3'5'H and DFR enzymes may be from any source including *Viola* sp, *Petunia* sp, *Salvia* sp, *Lisianthus* sp, *Gentiana* sp, *Sollya* sp, *Clitoria* sp, *Kennedia* sp, *Campanula* sp, *Lavandula* sp, *Verbena* sp, *Torenia* sp, *Delphinium* sp, *Solanum* sp, *Cineraria* sp, *Vitis* sp, *Babiana* stricta, *Pinus* sp, *Picea* sp, *Larix* sp, *Phaseolus* sp, *Vaccinium* sp, *Cyclamen* sp, *Iris* sp, *Pelargonium* sp, Liparieae, *Geranium* sp, *Pisum* sp, *Lathyrus* sp, *Catharanthus* sp, *Malvia* sp, *Mucuna* sp, *Vicia* sp, *Saintpaulia* sp, *Lagerstroemia* sp, *bouchina* sp, *Plumbago* sp, *Hypocalyptus* sp, *Rhododendron* sp, *Linum* sp, *Macroptilium* sp, *Hibiscus* sp, *Hydrangea* sp, *Cymbidium* sp, *Millettia* sp, *Hedysarum* sp, *Lespedeza* sp, *Asparagus* sp, *Antigonon* sp, *Pisum* sp, *Freesia* sp, *Brunella* sp or *Clarkia* sp, etc. Both F3'5'H enzymes may come from the same plant species or different plant species. For example, in one embodiment, the two F3'5'H enzymes come from *Viola* sp and *Salvia* sp. The DFR may come again from the same or different plant species.

The present invention further contemplates the use of genetic sequences encoding at least two F3'5'H enzymes and at least one DFR enzyme in the manufacture of a spray carnation such as a Kortina Chanel carnation or sports thereof exhibiting altered inflorescence including tissue having a purple to blue color.

In another embodiment, the present invention contemplates the use of genetic sequences encoding at least two F3'5'H enzymes and at least one DFR enzyme in the manufacture of a genetically modified plant selected from a rose, chrysanthemum, gerbera tulip, lily, orchid, lisianthus, begonia, torenia, geranium, petunia, nierembergia, pelargonium, iris, impatiens, cyclamen grape, apple, *Euphorbia* or *Fuchsia* or other ornamental or horticultural thereof exhibiting altered inflorescence including tissue having a purple to blue color.

Cut flowers, tissue culturable cells, regenerable cells, parts of plants, seeds, reproductive material (including pollen) are all encompassed by the present invention.

As indicated above, nucleotide sequences encoding F3'5'H and DFR enzymes may all come from the same species of plant or from two or more different species. F3'5'H nucleotide sequences from *Viola* sp and *Salvia* sp and a DFR from a *Petunia* sp are particularly useful in the practice of the present invention. The nucleotide sequences encoding the F3'5'H enzymes and the DFR enzyme and the respective amino acid sequences are defined in Table 1.

Nucleic acid molecules encoding F3'S'Hs are also provided in International Patent Application No. PCT/AU92/00334 and Holton et al, 1993 supra. These sequences have been used to modulate 3',5' hydroxylation of flavonoids in petunia (see International Patent Application No. PCT/AU92/00334 and Holton et al, 1993 supra), tobacco (see International Patent Application No. PCT/AU92/00334) and carnations (see International Patent Application No. PCT/AU96/00296). Nucleotide sequences of F3'5'H from other species such as *Viola*, *Salvia* and *Sollya* have been cloned (see International Patent Application No. PCT/AU03/01111). Any of these sequences may be used in combination with a promoter and/or terminator. The present invention particularly contemplates F3'5'H encoded by SEQ ID NOs:1, 3 and 9 and a DFR encoded by SEQ ID NO:5 or a nucleotide sequence capable of hybridizing to any of SEQ ID NOs:1, 3, 5 or 9 or a complementary form thereof under low or high stringency conditions or which has at least about 70% identity to SEQ ID NO:1 or 3 or 5 or 9 after optimal alignment. Terminator sequence SEQ ID NO:8 and promoter sequence SEQ ID NO:7 are also encompassed herein as well as sequences which hybridize thereto or have at least 70% similarity thereto For the purposes of determining the level of stringency to define nucleic acid molecules capable of hybridizing to SEQ ID NO:1, SEQ ID NO:3, SEQ ID NO:5, SEQ ID NO:7, SEQ ID NO:9 or their complementary forms, low stringency includes and encompasses from at least about 0% to at least about 15% v/v formamide and from at least about 1M to at least about 2 M salt for hybridization, and at least about 1 M to at least about 2 M salt for washing conditions. Generally, low stringency is from about 25-30° C. to about 42° C. The temperature may be altered and higher temperatures used to replace the inclusion of formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C) % (Marmur and Doty, *J. Mol. Biol.* 5:109, 1962). However, the $T_m$ of a duplex DNA decreases by 1° C. with every increase of 1% in the number of mismatch base pairs (Bonner and Laskey, *Eur. J. Biochem.* 46:83, 1974). Formamide is optional in these hybridization conditions. Accordingly, particularly preferred levels of stringency are defined as follows: low stringency is 6×SSC buffer, 1.0% w/v SDS at 25-42° C.; a moderate stringency is 2×SSC buffer, 1.0% w/v SDS at a temperature in the range 20° C. to 65° C.; high stringency is 0.1×SSC buffer, 0.1% w/v SDS at a temperature of at least 65° C.

Reference to at least 70% identity includes 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100% identity. The comparison may also be made at the level of similarity of amino acid sequences of SEQ ID NO:s:2, 4, 6 or 10. Hence, nucleic acid molecules are contemplated herein which encode an F3'5'H enzyme or DFR having at least 70% similarity to the amino acid sequence set forth in SEQ ID NOs:2 or 4 or 6 or 10. Again, at least 70% similarity includes 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100% similarity or identity.

The nucleic acid molecule encoding the F3'S'H enzymes and the DFR includes one or more promoters and/or terminators. In one embodiment, a promoter is selected which directs expression of a F3'S'H and/or a DFR nucleotide sequence in tissue having a higher pH.

In an embodiment, the promoter sequence is native to the host carnation plant to be transformed or may be derived from an alternative source, where the region is functional in the host plant. Other sources include the *Agrobacterium* T-DNA genes, such as the promoters for the genes encoding enzymes for biosynthesis of nopaline, octapine, mannopine, or other opines; promoters from plants, such as promoters from genes encoding ubiquitin; tissue specific promoters (see, e.g., U.S. Pat. No. 5,459,252 to Conkling et al; WO 91/13992 to Advanced Technologies); promoters from plant viruses (including host specific viruses), or partially or wholly synthetic promoters. Numerous promoters that are potentially functional in carnation plants (see, for example, Greve, *J. Mol. Appl. Genet.* 1:499-511, 1983; Salomon et al, *EMBO, J.* 3:141-146, 1984; Garfinkel et al, *Cell* 27:143-153, 1983; Barker et al, *Plant Mol. Biol.* 2:235-350, 1983); including various promoters isolated from plants (such as the Ubi promoter from the maize obi-1 gene, see, e.g., U.S. Pat. No. 4,962,028) and viruses (such as the cauliflower mosaic virus promoter, CaMV 35S). In other embodiments the promoter is AmCHS 5', carnANS 5' and/or petDFR 5' (from Pet gen DFR) with corresponding terminators petD8 3', carn ANS 3' and petDFR 3' (from Pet gen DFR), respectively.

The promoter sequences may include cis-acting sequences which regulate transcription, where the regulation involves, for example, chemical or physical repression or induction (e.g, regulation based on metabolites, light, or other physico-chemical factors; see, e.g, WO 93/06710 disclosing a nematode responsive promoter) or regulation based on cell differentiation (such as associated with leaves, roots, seed, or the like in plants; see, e.g. U.S. Pat. No. 5,459,252 disclosing a root-specific promoter).

Other cis-acting sequences which may be employed include transcriptional and/or translational enhancers. These enhancer regions are well known to persons skilled in the art, and can include the ATG initiation codon and adjacent sequences.

The nucleic acid molecule(s) encoding at least two F3'S'H enzymes and at least one DFR, in combination with suitable promoters and/or a terminators is/are used to modulate the activity of a flavonoid molecule in a spray carnation. Reference herein to modulating the level of a delphinidin-based molecule relates to an elevation or reduction in levels of up to 30% or more particularly of 30-50%, or even more particularly 50-75% or still more particularly 75% or greater above or below the normal endogenous or existing levels of activity.

The term "inflorescence" as used herein refers to the flowering part of a plant or any flowering system of more than one flower which is usually separated from the vegetative parts by an extended internode, and normally comprises individual flowers, bracts and peduncles, and pedicels. As indicated above, reference to a "transgenic plant" may also be read as a "genetically modified plant" and includes a progeny or hybrid line ultimately derived from a first generation transgenic plant.

The present invention also contemplates the use of genetic sequences encoding at least two F3'5'H enzymes and at least one DFR enzyme in the manufacture of a spray carnation such as a Kortina Chanel carnation or Cerise Westpearl carnation or sports thereof exhibiting altered inflorescence including tissue having a purple to blue color.

A cultivation business model is also provided, the model comprising generating a genetically modified spray carnation plant as described herein, providing platelets, seeds, regenerable cells, tissue culturable cells or other material to a grower, generating commercial sale numbers of plants, and providing cut flowers to retailers or wholesalers.

The present invention is further described by the following non-limiting Examples. In these Examples, materials and methods as outlined below were employed:

Methods followed were as described in Sambrook et al, *Molecular Cloning: A Laboratory Manual*, Cold Spring Harbor Laboratories, Cold Spring Harbor, N.Y., USA, 1989 or Sambrook and Russell, *Molecular Cloning: A Laboratory Manual* 3$^{rd}$ edition, Cold Spring Harbor Laboratories, Cold Spring Harbor, N.Y., USA, 2001 or *Plant Molecular Biology Manual* (2$^{nd}$ edition), Gelvin and Schilperoot (eds), Kluwer Academic Publisher, The Netherlands, 1994 or *Plant Molecular Biology Labfax*, Croy (ed), Bios scientific Publishers, Oxford, UK, 1993.

The cloning vectors pBluescript and PCR script were obtained from Stratagene, USA. pCR7 2.1 was obtained from Invitrogen, USA.

*E. coli* Transformation

The *Escherichia* coli strains used were:

DH5α supE44, Δ (lacZYA-ArgF)U169, (ø80lacZΔM15), hsdR17 ($r_k^-$, $m_k^+$), recA1, endA1, gyrA96, thi-1, relA1, deoR. (Hanahan, *J. Mol. Biol.* 166:557, 1983)

XL1-Blue supE44, hsdR17($r_k^-$, $m_k^+$), recA1, endA1, gyrA96, thi-1, relA1, lac$^-$, [F'proAB, lacI$^q$, lacZΔM15, Tn10 (tet$^R$)] (Bullock et al, *Biotechniques* 5:376, 1987).

BL21-CodonPlus-RIL Strain ompT hsdS(Rb− mB−) dcm+ Tet$^r$ gal endA Hte [argU ileY leuW Cam$^r$]

M15 *E. coli* is derived from *E. coli* K12 and has the phenotype Nal$^s$, Str$^s$, Rif$^s$, Thi$^-$, Ara$^+$, Gal$^+$, Mtl$^-$, F$^-$, RecA$^+$, Uvr$^+$, Lon$^+$.

Transformation of the *E. coli* strains was performed according to the method of Inoue et al, (*Gene* 96:23-28, 1990).

*Agrobacterium tumefaciens* trains and Transformations

The disarmed *Agrobacterium tumefaciens* strain used was AGL0 (Lazo et al, *Bio/technology* 9:963-967, 1991).

Plasmid DNA was introduced into the *Agrobacterium tumefaciens* strain AGL0 by adding 5 μg is of plasmid DNA to 100 μL of competent AGL0 cells prepared by inoculating a 50 mL LB culture (Sambrook et al, 1989 supra) and incubation for 16 hours with shaking at 28° C. The cells were then pelleted and resuspended in 0.5 mL of 85% (v/v) 100 mM CaCl$_2$/15% (v/v) glycerol. The DNA-Agrobacterium mixture was frozen by incubation in liquid N$_2$ for 2 minutes and then allowed to thaw by incubation at 37° C. for 5 minutes. The DNA/bacterial mix was then placed on ice for a further 10 minutes. The cells were then mixed with 1 mL of LB (Sambrook et al, 1989 supra) media and incubated with shaking for 16 hours at 28° C. Cells of *A. tumefaciens* carrying the plasmid were selected on LB agar plates containing appropriate antibiotics such as 50 μg/mL tetracycline or 100 μg/mL gentamycin. The confirmation of the plasmid in *A. tumefaciens* was done by restriction endonuclease mapping of DNA isolated from the antibiotic-resistant transformants.

DNA Ligations

DNA ligations were carried out using the Amersham Ligation Kit or Promega Ligation Kit according to procedures recommended by the manufacturer.

Isolation and Purification of DNA Fragments

Fragments were generally isolated on a 1% (w/v) agarose gel and purified using the QIAEX II Gel Extraction kit (Qiagen) or Bresaclean Kit (Bresatec, Australia) following procedures recommended by the manufacturer.

Repair of Overhanging Ends After Restriction Endonuclease Digestion

Overhanging 5' ends were repaired using DNA polymerase I Klenow fragment according to standard protocols (Sambrook et al, 1989 supra). Overhanging 3' ends were repaired using Bacteriophage T4 DNA polymerase according to standard protocols (Sambrook et al, 1989 supra).

Removal of Phosphoryl Groups from Nucleic Acids

Shrimp alkaline phosphatase (SAP) [USB] was typically used to remove phosphoryl groups from cloning vectors to prevent re-circularization according to the manufacturer's recommendations.

Polymerase Chain Reaction (PCR)

Unless otherwise specified, PCR conditions using plasmid DNA as template included using 2 ng of plasmid DNA, 100 ng of each primer, 2 µL, 10 mM dNTP mix, 5 µL, 10×Taq DNA polymerase buffer, 0.5 µL Taq DNA Polymerase in a total volume of 50 µL. Cycling conditions comprised an initial denaturation step of 5 minutes at 94° C., followed by 35 cycles of 94° C. for 20 sec, 50° C. for 30 sec and 72° C. for 1 minute with a final treatment at 72° C. for 10 minutes before storage at 4° C.

PCRs were performed in a Perkin Elmer GeneAmp PCR System 9600.

$^{32}$P-Labeling of DNA Probes

DNA fragments (50 to 100 ng) were radioactively labeled with 50 µCi of [α-$^{32}$P]-dCTP using a Gigaprime kit (Geneworks). Unincorporated [α-$^{32}$P]-dCTP was removed by chromatography on Sephadex G-50 (Fine) columns or Microbiospin P-30 Tris chromatography columns (BioRad).

Plasmid Isolation

Single colonies were analyzed for inserts by inoculating LB broth (Sambrook et al, 1989 supra) with appropriate antibiotic selection (e.g. 100 µg/mL ampicillin or 10 to 50 µg/mL tetracycline etc.) and incubating the liquid culture at 37° C. (for *E. coli*) or 29° C. (for *A. tumefaciens*) for ~16 hours with shaking. Plasmid DNA was purified using the alkali-lysis procedure (Sambrook et al, 1989 supra) or using The Wizard-Plus SV minipreps DNA purification system (Promega) or Qiagen Plasmid Mini Kit (Qiagen). Once the presence of an insert had been determined, larger amounts of plasmid DNA were prepared from 50 mL overnight cultures using the alkali-lysis procedure (Sambrook et al, 1989 supra) or QIA-filter Plasmid Midi kit (Qiagen) and following conditions recommended by the manufacturer.

DNA Sequence Analysis

DNA sequencing was performed using the PRISM (trademark) Ready Reaction Dye Primer Cycle Sequencing Kits from Applied Biosystems. The protocols supplied by the manufacturer were followed. The cycle sequencing reactions were performed using a Perkin Elmer PCR machine (GeneAmp PCR System 9600). Sequencing runs were generally performed by the Australian Genome Research Facility at the University of Queensland, St Lucia, Brisbane, Australia and at The Walter and Eliza Hall Institute of Medical Research (Melbourne, Australia) or on an automated 373A DNA sequencer (Applied Biosystems).

Sequences were analysed using a MacVector (Trade mark) application (version 9.5.2 and earlier) [MacVector Inc, Cary, N.C., USA].

Homology searches against Genbank, SWISS-PROT and EMBL databases were performed using the FASTA and TFASTA programs (Pearson and Lipman, *Proc. Natl. Acad. Sci. USA* 85 (8):2444-2448, 1988) or BLAST programs (Altschul et al, *J. Mol. Biol.* 215 (3):403-410, 1990). Percentage sequence similarities were obtained using LALIGN program (Huang and Miller, *Adv. Appl. Math.* 12:373-381, 1991) or ClustalW program (Thompson et al, *Nucleic Acids Research* 22:4673-4680, 1994) within the MacVector (Trade mark) application (MacVector Inc, USA) using default settings.

Multiple sequence alignments were produced using ClustalW (Thompson et al, 1994 supra) using default settings.

Plant Transformations

Plant transformations were as described in International Patent Application No. PCT/US92/02612 incorporated herein by reference or International Patent Application No. PCT/AU96/00296 or Lu et al, *Bio/Technology* 9:864-868, 1991. Other methods may also be employed.

Cuttings of *Dianthus caryophyllus* cv. Kortina Chanel were obtained from Van Wyk and Son Flower Supply, Victoria or Propagation Australia, Queensland, Australia.

Transgenic Analysis

Color Coding

The Royal Horticultural Society's Color Charts, Third and/or Fifth edition (London, UK), 1995 and/or 2007 were used to provide a description of observed color. They provide an alternative means by which to describe the color phenotypes observed. The designated numbers, however, should be taken only as a guide to the perceived colors and should not be regarded as limiting the possible colors which may be obtained.

Carnation petals consist of 3 zones, the claw, corona and limb (Glimn-Lacy and

Kaufman, Botany Illustrated, Introduction to Plants, Major Groups, Flowering Plant Families, $2^{nd}$ ed, Springer, USA, 2006). In general only the petal limb is colored with the claw being a green color and the corona a white shade (see FIG. 4). Reference to carnation petal/flower/inflorescence color generally relates to the color of the carnation petal limb.

Chromatographic Analysis

Thin Layer Chromatography (TLC) and High Performance Liquid Chromatography (HPLC) analysis was performed generally as described in Brugliera et al, (*Plant J.* 5:81-92, 1994).

In general TLC and HPLC analysis was performed on extracts isolated from the petal limbs.

Extraction of Anthocyanidins

Prior to HPLC analysis, the anthocyanin and flavonol molecules present in petal limbextracts were acid hydrolysed to remove glycosyl moieties from the anthocyanidin or flavonol core. Anthocyanidin and flavonol standards were used to help identify the compounds present in the floral extracts.

Anthocyanidins in the reaction mixture were analysed by HPLC via gradient elution using gradient conditions of 50% B to 60% B over 10 minutes, then 60% B for 10 minutes and finally 60% B to 100% B over 5 minutes where solvent A consisted of TFA:$H_2O$ (5:995) and solvent B consisted of acetonitrile: TFA:$H_2O$ (500:5:495). An Asahi Pac ODP-50 cartridge column (250 mm×4.6 mm ID) was used for the reversed phase chromatographic separations. The flow rate was 1 mL/min and the temperature was 40° C. The detection of the anthocyanidin compounds was carried out using a Shimadzu SPD-M6A three dimensional detector at 400-650 nm.

The anthocyanidin peaks were identified by reference to known standards, viz delphinidin, petunidin, malvidin, cyanidin and peonidin Stages of Flower Development Carnation flowers were harvested at developmental stages defined as follows:

Stage 1: Closed bud, petals not visible.
Stage 2: Flower buds opening: tips of petals visible.
Stage 3: Tips of nearly all petals exposed. "Paint-brush stage".
Stage 4: Outer petals at 45° angle to stem.
Stage 5: Flower fully open.

For TLC or HPLC analysis, petal limbs were collected from stage 4 flowers at the stage of maximum pigment accumulation.

For Northern blot analysis, petals were collected from stage 3 flowers at the stage of maximal expression of flavonoid pathway genes.

Example 1

Preparation of Chimeric F3'5'H Gene Constructs

A summary of promoter, terminator and coding fragments used in the preparation of constructs and the respective abbreviations is listed in Table 2.

TABLE 2

Abbreviations used in construct preparations

| ABBREVIATION | DESCRIPTION |
| --- | --- |
| 35S 5' | promoter fragment from CaMV 35S gene (Franck et al, 1980 supra) with an ~60 bp 5' untranslated leader sequence (CabL) from the *petunia* chlorophyll a/b binding protein gene (Cab 22 gene) [Harpster et al, MGG, 212: 182-190, 1988] |
| AmCHS 5' | Promoter fragment from the *Antirrhinum majus* chalcone synthase (CHS) gene which includes 1.2 kb sequence 5' of the translation initiation site (Sommer and Saedler, Mol Gen. Gent., 202: 429-434, 1986) |
| BPF3'5'H#18 | *Viola* (Black Pansy) F3'5'H cDNA clone #18 (International Patent Application No. PCT/AU03/01111) [SEQ ID NO: 1] |
| BPF3'5'H#40 | *Viola* (Black Pansy) F3'5'H cDNA clone #40 (International Patent Application No. PCT/AU03/01111 incorporated herein by reference) |
| CaMV 35S | ~0.2 kb incorporating BglII fragment containing the promoter region from the Cauliflower Mosaic Virus 35S (CaMV 35S) gene - (Franck et al, Cell 21: 285-294, 1980, Guilley et al, Cell, 30: 763-773. 1982) |
| carnANS 3' | Terminator sequence of anthocyanidin synthase gene (ANS) from *Dianthus caryophyllus* (See International Patent Application No. PCT/GB99/02676 incorporated herein by reference) [SEQ ID NO: 8] |
| carnANS 5' | Promoter sequence of anthocyanidin synthase (ANS) gene from *Dianthus caryophyllus* (See International Patent Application No. PCT/GB99/02676) [SEQ ID NO: 7] |
| Pet CHS-A 5' | Promoter region of the *Petunia hybrida* CHS-A gene (Van der Meer et al, Plant Mol Biol 15: 95-109, 1990) |
| Pet gen DFR | ~5.3 kb *Petunia* DFR-A genomic clone with it's own promoter and terminator (SEQ ID NO: 5) |
| petD8 3' | ~0.7 kb terminator region from a phospholipid transfer protein gene (D8) of *Petunia hybrida* cv. OGB includes a 150 bp untranslated region of the transcribed region of PLTP gene (Holton, Isolation and characterization of petal-specific genes from *Petunia hybrida*. PhD Thesis, University of Melbourne, 1992) |
| petHf1 | *Petunia* F3'5'H Hf1 cDNA clone (Holton et al, 1993 supra) |
| *Salvia*F3'5'H#2 | *Salvia* F3'5'H cDNA clone #2 (International Patent Application No. PCT/AU03/01111 incorporated herein by reference) |
| *Salvia*F3'5'H#47 | *Salvia* F3'5'H cDNA clone #47 (International Patent Application No. PCT/AU03/01111) [SEQ ID NO: 3] |
| *Sollya*F3'5'H | *Sollya* F3'5'H cDNA clone (International Patent Application No. PCT/AU03/01111) |
| SuRB | Herbicide (Chlorsulfuron)-resistance gene (encodes Acetolactate Synthase) with its own terminator (tSuRB) from *Nicotiana tabacum* (Lee et al, EMBO J. 7: 1241-1248, 1988) |
| RoseCHS 5' | ~2.8 kb fragment containing the promoter region from a CHS gene of *Rosa hybrida* (see International Patent Application No. PCT/AU03/01111 incorporated herein by reference) |
| nos 3' | Terminator region from the nopaline synthase (nos) gene of *A. tumefaciens* (Depicker et al, J Mol. and Appl. Genetics 7: 561-573, 1982) |

Kortina Chanel is a light pink colored (RHS color codes 65A, 65A, 65C, 73B, 73C, 73D) carnation of the spray type. It typically accumulates cyanidin-based pigments (0.08 mg/g petal fresh weight) and a mixture of quercetin and kaempferol flavonols (5.3 mg/g and 4.6 mg/g petal fresh weight respectively). Kortina Chanel can also sport to darker purple-pink colored flower (RHS color codes 64A, 61A, 71A) [Kortina] with cyanidin derivatives typically accumulating to levels 10 fold higher than the original.

In order to produce novel purple/blue flowers in the spray carnation background of Kortina Chanel, a number of binary vector constructs were prepared utilizing the petunia, pansy, salvia, sollya and butterfly pea F3'5'H cDNA fragments and various promoter and terminator fragments. The chimeric F3'5'H genes had proved successful in other carnations and petunia leading to detectable intact F3'5'H transcripts (as detected by Northern blot analysis) and to the production of delphinidin or delphinidin-based molecules pigments. Table 3 summarizes the list of binary vector constructs containing F3'5'H cDNA fragments.

TABLE 3

Summary of chimeric F3'5'H and DFR gene expression cassettes contained in binary vector constructs used in the transformation of Kortina Chanel

| PLASMID | F3'5'H & DFR GENE(S) | SELECTABLE MARKER GENE |
|---|---|---|
| pCGP1452 | AmCHS 5':petHfl:petD8 3' | 35S 5':SuRB |
| pCGP1972 | AmCHS 5':BPF3'5'H#18:petD8 3' | 35S 5':SuRB |
| pCGP1973 | AmCHS 5':BPF3'5'H#40:petD8 3' | 35S 5':SuRB |
| pCGP1991 | AmCHS 5':BPF3'5'H#40:ocs 3'; Pet gen DFR | 35S 5':SuRB |
| pCGP2121 | AmCHS 5':*Salvia*F3'5'H#2:petD8 3' | 35S 5':SuRB |
| pCGP2122 | AmCHS 5':*Salvia*F3'5'H#47:petD8 3' | 35S 5':SuRB |
| pCGP2130 | AmCHS 5':*Sollya*F3'5'H:petD8 3' | 35S 5':SuRB |
| pCGP2205 | carnANS 5':BPF3'5'H#18:carnANS 3' | 35S 5':SuRB |

(see Table 2 for an explanation of abbreviations)

The Transformation Vectors, pCGP1452, pCGP1972, pCGP1973, pCGP2121, pCGP2122, pCGP2130

The preparation of the transformation vectors pCGP1452, pCGP1972, pCGP1973, pCGP2121, pCGP2122, pCGP2130 are described in International Patent Application No. PCT/AU03/01111.

The Transformation Vector, pCGP1991

The transformation vector pCGP 1991 contains the AmCHS 5 BPF3'5'H#40:ocs 3' expression cassette and the petunia genomic DFR-A gene along with the 35S 5':SuRB selectable marker gene.

Construction of the Intermediate Plasmid, pCGP1472 (*Petunia* DFR-A Genomic Clone)

A genomic library was made from *Petunia hybrida* cv. Old Glory Blue DNA in the vector λ2001 (Holton, 1992 supra). Approximately 200,000 pfu were plated out on NZY plates, lifts were taken onto NEN filters and the filters were hybridized with 400,000 cpm/mL of $^{32}$P-labeled petunia DFR-A cDNA fragment (described in Brugliera et al, 1994, supra). Hybridizing clones were purified, DNA was isolated from each and mapped by restriction endonuclease digestion. A 13 kb Sad fragment of one of these clones was isolated and ligated with Sad ends of pBluescriptII to create the plasmid pCGP1472. Finer mapping indicated that an ~5.3 kb BglII fragment contained the entire petunia DFR gene (Beld et al, *Plant Mol. Biol.* 13:491-502, 1989).

Construction of Intermediate Plasmid, pCGP1984 (pet gen DFR:35S 5':SuRB)

The plasmid pCGP1984 contains the petunia genomic DFR-A gene (Pet gen DFR) along with the 35S 5':SuRB selectable marker gene in the pWTT2132 (DNAP) backbone.

The plasmid pCGP1472 (described above) was digested with the restriction endonuclease (RE) BglII to release a ~5.3 kb fragment containing the entire petunia DFR-A gene. The resulting 5'-overhang was repaired using DNA Polymerase I (Klenow fragment) according to standard protocols (Sambrook et al, 1989 supra). The vector pWTT2132 (DNAP) was digested with the RE KpnI to linearize the vector. The resulting overhanging 3'-ends of the vector were removed with Bacteriophage T4 DNA polymerase according to standard protocols (Sambrook et al, 1989 supra). The 5.3kb fragment containing the petunia DFR-A gene was ligated with the repaired KpnI ends of the vector pWTT2132. Successful ligation of the fragment in the desired orientation in pWTT2132 was established by RE digestion of plasmid DNA isolated from tetracycline resistant *E. coli* transformants. The resulting plasmid was designated as pCGP1984.

Construction of Intermediate Plasmid, 1971 (AmCHS 5': BPF3'5'H#40:petD8 39

The plasmid pCGP1971 contains a chimeric gene consisting of AmCHS 5': BPF3'5'H#40:petD8 3' in a pBluescript backbone. Construction of pCGP1971 is described in International Patent Application No. PCT/AU03/01111.

Construction of the Transformation Vector pCGP1991 (Am CHS 5': BPF3'5'H#40:petD8 3'; Pet gen DFR; 35S 5':SuRB)

The plasmid pCGP1971 was digested with REs EcoRV/NotI to release a 3.5 kb fragment containing a chimeric AmCHS 5':BPF3'57-1#40:petD8 3' gene. The resulting 5'-overhang was repaired using DNA Polymerase I (Klenow fragment) according to standard protocols (Sambrook et al, 1989 supra). The fragment was purified and ligated with repaired PstI ends of the linearized plasmid pCGP 1984 (described above). Correct insertion of the AmCHS 5':BPF3'5'H#40:petD8 3' fragment in pCGP1984 was established by restriction endonuclease digestion of plasmid DNA isolated from tetracycline resistant *E. coli* transformants. The resulting transformation vector was designated as pCGP 1991.

The Transformation Vector pCGP2205 (carnANS 5': BPF3'5'H#18:carnANS 3)

The transformation vector pCGP2205 contains a chimeric carnANS 5': BPF3'5'H#18:carnANS 3' gene cassette in tandem with the 35S 5':SuRB selectable marker gene cassette of the plasmid pCGP1988 (see International Patent Application No. PCT/AU03/01111).

Construction of Intermediate Plasmid, pCGP787. Isolation of Carnation ANS Genomic Clone A genomic DNA library was constructed from *Dianthus caryophyllus* cv. Laguna DNA in EMBL 3 lambda vector (STRATAGENE) using a Sau3A partial digest. The digested genomic DNA was size fractionated on a glycerol density gradient and fractions containing DNA fragments ranging from 15 to 20kb were pooled and ligated with BamHI ends of EMBL3 λ vector. The ligation mixture was packaged using Gigapack XL Gold (PROMEGA). The total size of the library was 1×10$^6$ recombinants.

A total of 300,000 pfu of the Laguna genomic library were screened in duplicate with $^{32}$P-labeled fragments of carnation ANS cDNA clone from pCGP786 (see International Patent Application No. PCT/AU96/00296). Hybridization was carried using high stringency conditions (42° C., 50% formamide, 0.1% PVP, 0.1% BSA, 0.1% ficoll, 1% SDS, 100 μg/mL denatured herrung sperm DNA. Washes were 2×SSC/

1% SDS and 0.2×SSC/1% SDS at 65° C. A genomic clone (4.3) was subsequently purified and further characterized. An 8 kb HindIII fragment of the genomic clone was subcloned into pBluescript KS for further analysis. The resulting plasmid was designated pCGP787.

Construction of Intermediate Plasmid, pCGP1274 (ANS Promoter Fragment)

A ~2.5 kb fragment containing promoter sequences from the carnation ANS gene was released from pCGP787 (described above) upon digestion with the REs EcoRI and BamHI. The fragment was purified and ligated with EcoRI/BamHI ends of pBluescript KS to give the plasmid pCGP793. This 2.5 kb fragment included 200 bp of ANS coding sequence. The 3' end of the promoter fragment was then amplified by PCR using primers that introduced an XbaI site 5' upstream from the AUG codon. This 700 by PCR fragment was then digested with REs NdeI/XbaI and ligated with NdeI/XbaI ends of pCGP793 (described above) to produce a 2.3 kb ANS promoter fragment without the 200 bp of ANS coding sequence. This new plasmid was designated as pCGP 1274.

ANS 3') to produce the plasmid, pCGP2150 (containing the carnANS 5': BPF3'5'H#18:carnANS 3' expression cassette).

Construction of the Transformation Vector, pCGP2205

The chimeric carnANS 5': BPF3'5'H#18:carnANS 3' gene was released from pCGP2150 (described above) upon digestion with the RE ClaI. The ClaI ends of the ~4.8 kb fragment were repaired and the fragment was isolated, purified and ligated with repaired Asp718 I ends of the plasmid pCGP1988 (see International Patent Application No. PCT/AU03/01111). Correct insertion of carnANS 5': BPF3'5'H#18:carnANS 3' gene in a tandem orientation with respect to the 35S 5':SuRB selectable marker gene cassette was established by restriction endonuclease analysis of plasmid DNA isolated from tetracycline-resistant transformants. The transformation vector was designated as pCGP2205.

Results of transgenic analysis of petals from Kortina Chanel carnations carrying the gene expression cassettes of Table 3 are shown in Table 4.

TABLE 4

Results of transgenic analysis of petals from Kortina Chanel carnations transformed with T-DNAs containing F3'5'H gene expression cassettes.

| transgenes | pCGP | #tg | TLC+ | HPLC+ | Highest % del | RHSCC | RHSCC Group |
|---|---|---|---|---|---|---|---|
| AmCHS 5':petHf1:petD8 3' | 1452 | 104 | 41/64 | nd | 3.5% | No change | Red-Purple |
| AmCHS 5':BP F3'5'H #18:petD8 3' | 1972 | 26 | 18/20 | 12/12 | 25% | 71a | Red-Purple |
| AmCHS 5':BP F3'5'H #40:petD8 3' | 1973 | 26 | 11/15 | 7/8 | 18% | 71a, 74a | Red-Purple |
| AmCHS 5':BP F3'5'H #40:ocs 3'; Pet gen DFR | 1991 | 22 | 13/19 | 3/3 | 14% | 74a | Red-Purple |
| AmCHS 5':*Salvia* F3'5'H #2:petD8 3' | 2121 | 22 | 2/16 | 3/4 | 12.5% | 74a | Red-Purple |
| AmCHS 5':*Salvia* F3'5'H #47:petD8 3' | 2122 | 23 | 6/12 | 8/8 | 29% | 74a | Red-Purple |
| AmCHS 5':*Sollya* F3'5'H:petD8 3' | 2130 | 30 | 22/27 | 17/17 | 35% | 61a, 71a | Red-Purple |
| carnANS 5':BP F3'5'H #18:carnANS 3' | 2205 | 37 | 22/33 | 14/15 | 52% | 74a | Red-Purple |

Transgenes = chimeric F3'5'H and DFR nucleotide sequences contained on the T-DNA
pCGP = plasmid pCGP identification number of the transformation vector used in the transformation experiment (refer to Table 3 for details)
tg = total number of transgenic carnation lines produced
TLC+ = number of individual events in which delphinidin was detected in petals (as determined visually after TLC of petal extracts) over the total number of individual events analyzed
HPLC+ = number of individual events in which delphinidin was detected in petals (as determined by HPLC) over the total number of individual events analyzed
Highest % del = Highest % delphinidin detected in the petals for the population of transgenic events
nd = not done
RHSCC = The petal color of the flower with the highest delphinidin levels using color codes according to Royal Horticultural Society Color Chart Construction of Intermediate Plasmid, pCGP1275 (carnANS 5': carnANS 3' Cassette)

The plasmid pCGP795 (described above) was digested with the REs Ecl1136II/XbaI to release a 0.7 kb ANS terminator fragment. The fragment was purified and ligated with ApaI (blunted)/XbaI ends of pCGP1274 to produce the plasmid pCGP1275 (containing promoter and terminator sequences of the carnation ANS gene (carnANS 5': carnANS 3').

Construction of Intermediate Plasmid, pCGP2150 (carnANS 5': BPF3'5'H#18:carnANS 3' Cassette)

The plasmid pCGP1959 (containing a BPF3'5'H#18 cDNA clone) [described in see International Patent Application No. PCT/AU03/01111] was digested with the REs BamHI and Asp718. The ends were repaired and the purified BPF3'5'H#18 bearing fragment was ligated with the repaired PstI/XbaI ends of pCGP 1275 (containing carnANS 5':carn The results suggest that all of the F3'5'H sequences evaluated were stable in carnation and resulted in the production of novel delphinidin-based pigments in carnation flowers. However none of the constructs led to the production of >80% delphinidin or a novel commercially viable color change in the Kortina Chanel spray carnation variety. The color changes were all in the Red-Purple group of the RHS Color Chart.

Although over 290 transgenic Kortina Chanel spray carnations were produced (Table 4) none produced flowers with a change in color to purple/blue. The most dramatic change in color was to a red/purple color (RHS color codes 74a, 78a) that was not a commercially viable novel color. Although delphinidin-based pigments were produced they were at too low a level to modify the color to a commercially viable novel Violet, Purple-Violet, Purple/Blue.

Even the use of a chimeric F3'5'H and a petunia DFR gene (contained in pCGP1991, see Table 4) as has been used successfully in the modification of white carnations (deficient in DFR) [see International Patent Application No. PCT/AU96/00296] did not lead to the production of >80% delphinidin based pigments or a novel Violet, Purple-Violet, Purple-Blue color in the Kortina Chanel background.

Example 2

Delphinidin-based Anthocyanins

In order to increase the levels of delphinidin-based anthocyanins and therefore increase the chance of violet/purple/blue color in the Kortina Chanel spray carnation flowers, a novel construct was prepared that included the use of 2 (two) F3'5'H chimeric genes and a petunia DFR gene.

The DFR genomic fragments used in this application were isolated from petunia. The petunia DFR enzyme is only capable of using dihydroquercetin and dihydomyricetin as a substrate, but not dihydrokaempferol (Holton and Cornish, 1995 supra). This ensures that most or all of the anthocyanidin produced is delphinidin.

The F3'5'H coding sequences in the chimeric genes used in the new construct were from pansy (carnANS 5':BP F3'5'H #18: carnANS 3' in pCGP2205) and salvia (AmCHS 5': Salvia F3'5'H #47: petD8 3' in pCGP2122) [Table 3] as these represent the two expression cassettes that were the most efficient in producing the highest levels of delphinidin in the Kortina Chanel spray carnation so far (Table 4).

The Transformation Vector, pCGP2442

The transformation vector pCGP2442 (FIG. 2) contains a chimeric AmCHS:Salvia F3'5'H#47: petD8 3' gene in tandem with a petunia genomic DFR-A gene, a chimeric carnANS: BPF3'5'H#18:carnANS 3' gene and the 35S 5':SuRB selectable marker gene cassette of the plasmid pWTT2132 (see International Patent Application No. PCT/AU03/01111).

Construction of the Intermediate Plasmid, pCGP2221 (5.3 kb Petunia DFR-A Genomic Clone)

The plasmid pCGP2221 contains the petunia DFR-A gene (Pet gen DFR) from pCGP1472 (described above) in the cloning vector pNEB193 (NEW ENGLAND BIOLABS).

The plasmid pCGP1472 (described above in Example 1) was digested with the RE BglII to release a ~5.3 kb fragment containing the Pet gen DFR gene. The resulting 5'-overhang was partially repaired according to standard protocols (Sambrook et al, 1989 supra). The cloning vector pNEB 193 (DNAP) was digested with SalI to linearize the vector. The resulting overhanging ends of the vector were partially repaired according to standard protocols (Sambrook et al, 1989 supra). The 5.3 kb fragment bearing the Pet gen. DFR gene was ligated with the partially repaired ends of the vector pNEB193. Successful ligation in the desired orientation of the insert in pNEB 193 was established by restriction endonuclease digestion of plasmid DNA isolated from ampicillin-resistant E. coli transformants. The resulting plasmid was designated as pCGP2221.

Construction of the Intermediate Plasmid, pCGP2117 (AmCHS 5': Salvia F3'5'H#47:petD8 3' in pBluescript)

The plasmid pCGP2117 contains a AmCHS 5': Salvia F3'5'H#47:petD8 3' Expression Cassette in the Cloning Vector, pBluescript KSII. (Stratagene, USA).

The petunia F3'5'H (petHf1) cDNA clone in pCGP725 (contains AmCHS 5': petHf1:petD8 3' in a pBluescript KS backbone) [described in International Patent Application No. PCT/AU03/01111] was released by initially digesting the plasmid pCGP725 with the RE BamHI. The overhanging ends were repaired and the linearized plasmid was further digested with the RE XbaI. The ~4.9 kb fragment containing the vector with the AmCHS 5' and petD8 3' sequences was purified and ligated with the repaired ends of ~1.6 kb XhoI/EcoRI fragment from the plasmid pCGP1999 (containing the salvia F3'5'H #47 cDNA clone, described in International Patent Application No. PCT/AU03/01111), to produce the plasmid, pCGP2117.

Construction of the Intermediate Plasmid, pCGP2122 (AmCHS 5': salvia F3'5'H#47:petD8 3'; 35S: SuRB)

The plasmid pCGP2122 contains the AmCHS 5': salvia F3'5'H#47:petD8 3' expression cassette in tandem with the 35S 5': SuRB selectable marker gene.

The plasmid pCGP2117 (described above) was firstly linearized by digestion with the RE NotI. The ends of the linearized plasmid were repaired and then the AmCHS 5': salvia F3'5'H#47:petD8 3' cassette was released upon digestion with the RE EcoRV. The ~3.6 kb purified fragment was then ligated with the repaired Asp718 ends of the plasmid pCGP 1988 (described in International Patent Application No. PCT/AU03/01111). Successful ligation of the fragment in the desired orientation was established by restriction endonuclease analysis of plasmid DNA isolated from tetracycline-resistant transformants. The resulting plasmid was designated pCGP2122.

Construction of the Intermediate Plasmid, pCGP2438

The construct pCGP2438 contains AmCHS 5': SalviaF3'5'H#47:petD8 3', carnANS 5': BPF3'5'H#18:carnANS 3' and 35S 5':SuRB cassettes.

The carnANS 5': BPF3'5'H#18:carnANS 3' cassette contained in pCGP2150 (described above) was released upon digestion with the RE ClaI. The fragment was isolated, purified and ligated with SalI "T-filled" ends of pCGP2122 (containing AmCHS: SalviaF3'5'H#47:petD8 3' and 35S 5':SuRB cassettes) [described above]. Successful ligation of the fragment in the desired orientation was established by restriction endonuclease analysis of plasmid DNA isolated from tetracycline-resistant transformants. The resulting plasmid was designated pCGP2438.

Construction of the Transformation Vector, pCGP2442

The transformation vector pCGP2442 contains the chimeric AmCHS: Salvia F3'5'H#47.petD8 3' gene in tandem with Pet gen DFR, and carnANS 5': BPF3'5'H#18:carnANS 3' genes and the 35S 5':SuRB selectable marker gene.

Figure 2:
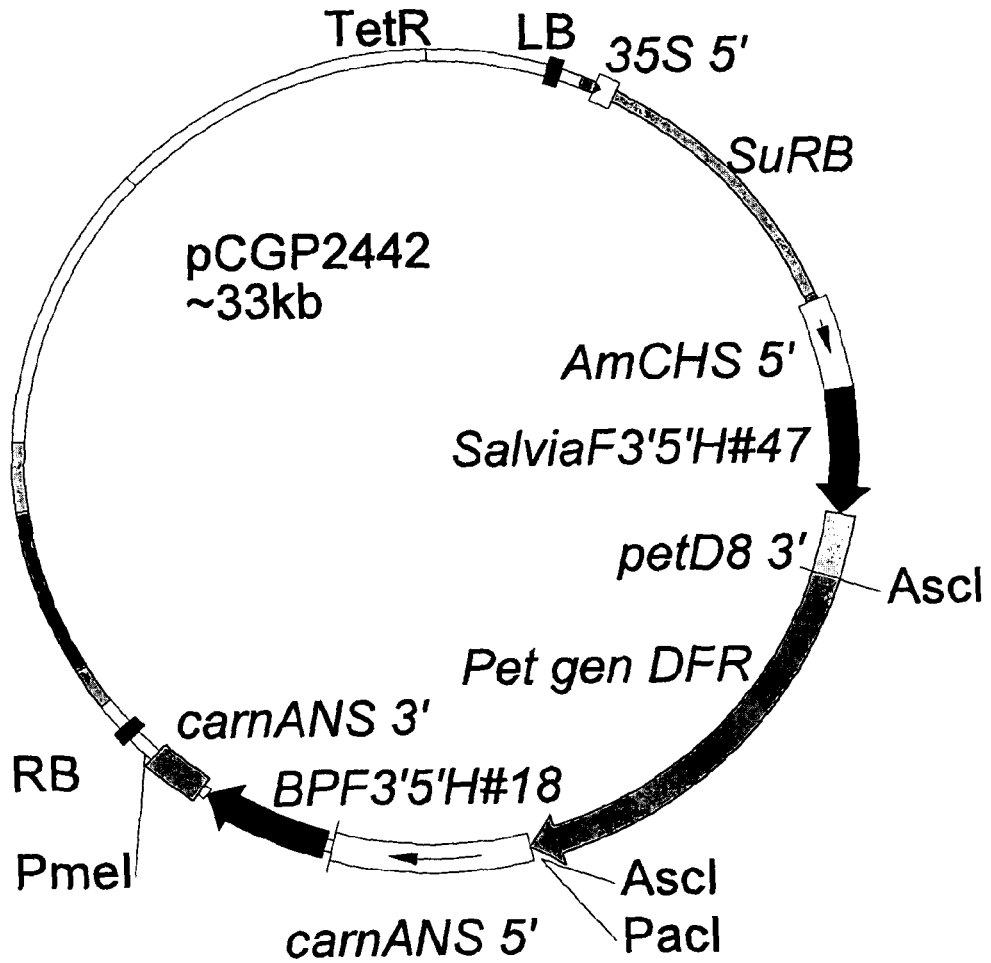
FIG. 2 is a diagrammatic representation of the binary plasmid pCGP2442. chimeric. The construction of pCGP2442 is described in Example 1. Selected restriction endonuclease sites (AscI, PacI PmeI) are marked. Abbreviations include LB=Left Border from *A. tumefaciens* Ti plasmid, RB=Right border region from *A. tumefaciens* Ti plasmid, TetR=antibiotic, tetracycline resistance gene complex Refer to Table 2 for a description of gene elements.

The Pet gen DFR clone from the plasmid pCGP2300 (described above) was released upon digestion with the RE AscI. The purified 5.3 kb fragment was then ligated with AscI ends of the plasmid pCGP2438 (described above). Successful ligation of the fragment in the desired orientation was established by restriction endonuclease analysis of plasmid DNA isolated from tetracycline-resistant transformants. The resulting transformation vector was designated pCGP2442 (FIG. 2).

TABLE 5

Chimeric F3'5'H and DFR genes contained in pCGP2442

| PLASMID | F3'5'H and DFR GENES | SELECTABLE MARKER GENE |
| --- | --- | --- |
| pCGP2442 | Pet gen DFR; carnANS 5':BPF3'5'H# 18:carnANS 3'; AmCHS 5':Salvia F3'5'H#47:pet D8 3' | CaMV 35S 5':SuRB |

The two chimeric F3'5'H genes and a DFR gene contained within the T-DNA of the transformation vector pCGP2442 was introduced into the spray carnation variety Kortina Chanel via Agrobacterium-mediated transformation.

Of 74 transgenic lines produced, eight produced flowers of a significant shift in color (RHSCC 71A, 71C, 72A, 81A, 86A, 87A; see Table 6). HPLC analysis of these lines revealed 30-94% delphinidin (up to 3.4 g delphinidin per gram fresh weight tissue). However, of the eight only three lines (19890, 19907 and 19898) [Table 6] produced flowers with a shift in color into the violet, purple/violet range and represented a commercially valuable, novel phenotype in a spray carnation (Kortina Chanel) background.

TABLE 6

Transgenic Kortina Chanel lines and the RHS color code of the petal limb

| ACCESSION NUMBER | RHSCC NUMBER (PETAL LIMB COLOR) | RHSCC GROUP |
|---|---|---|
| 19890 | 86A | VIOLET |
| 19942 | 71A | RED-PURPLE |
| 19898 | 87A | VIOLET |
| 19912 | 72A | RED-PURPLE |
| 19900 | 71A | RED-PURPLE |
| 19940 | 71A | RED-PURPLE |
| 19923 | 71C | RED-PURPLE |
| 19907 | 81A | PURPLE-VIOLET |

Description of Phenotypes

Figure 3:
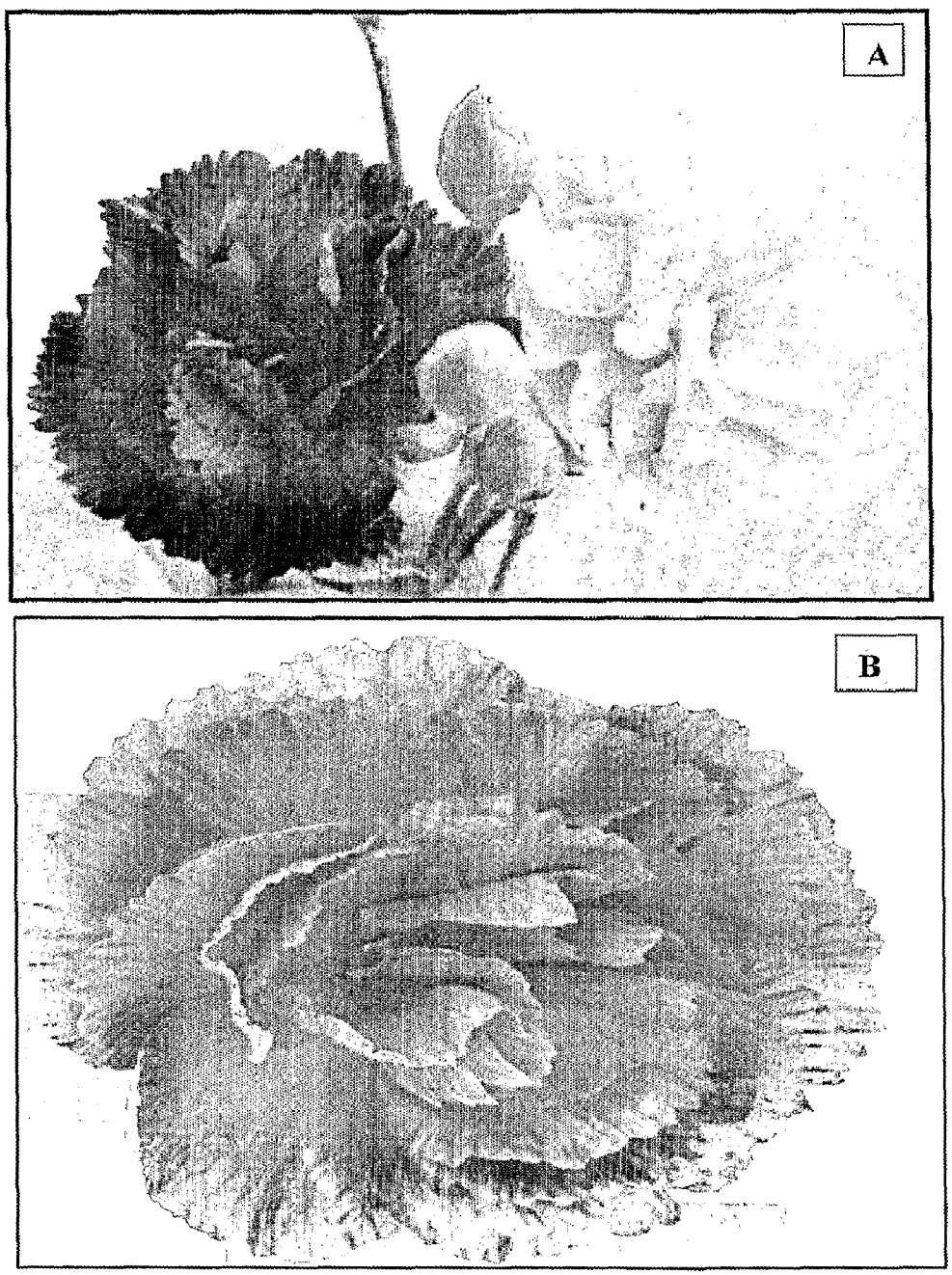
FIG. 3 is a photographic representation showing flowers from transgenic Kortina Chanel/pCGP2442 spray carnation lines. A: flowers from transgenic line 19890 (left hand side) and Kortina Chanel non-transgenic control (right-hand side); B: flower from transgenic line 19907.
Figure 4:
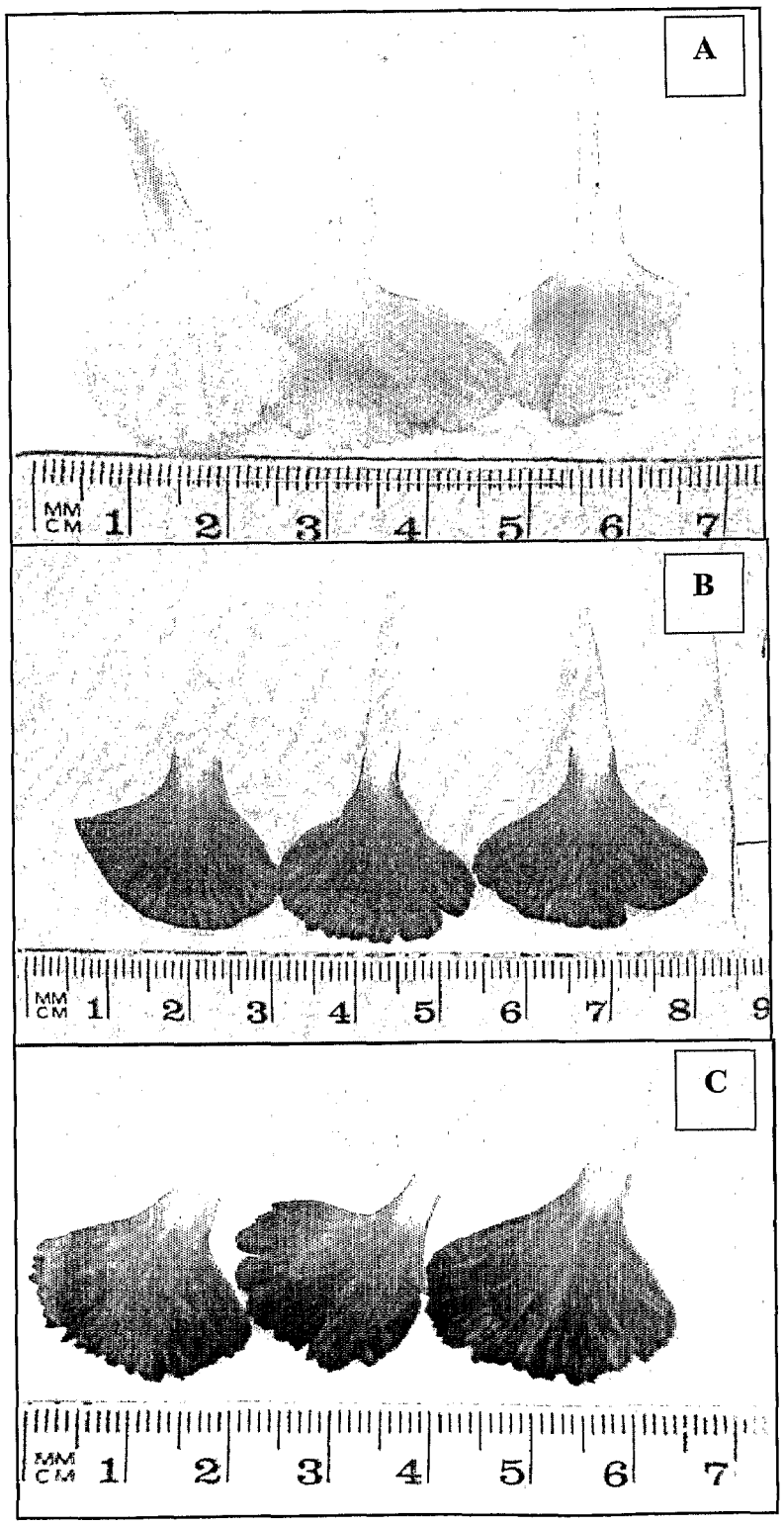
FIG. 4 is a photographic representation showing petal size and shape of Kortina Chanel/pCGP2442 spray carnation lines. A: petals from Kortina Chanel non-transgenic control flower; B: petals from flowers of the transgenic Kortina Chanel/pCGP2442 line 19907; C: petals from flowers of the transgenic Kortina Chanel/pCGP2442 line 19890.
Figure 5:
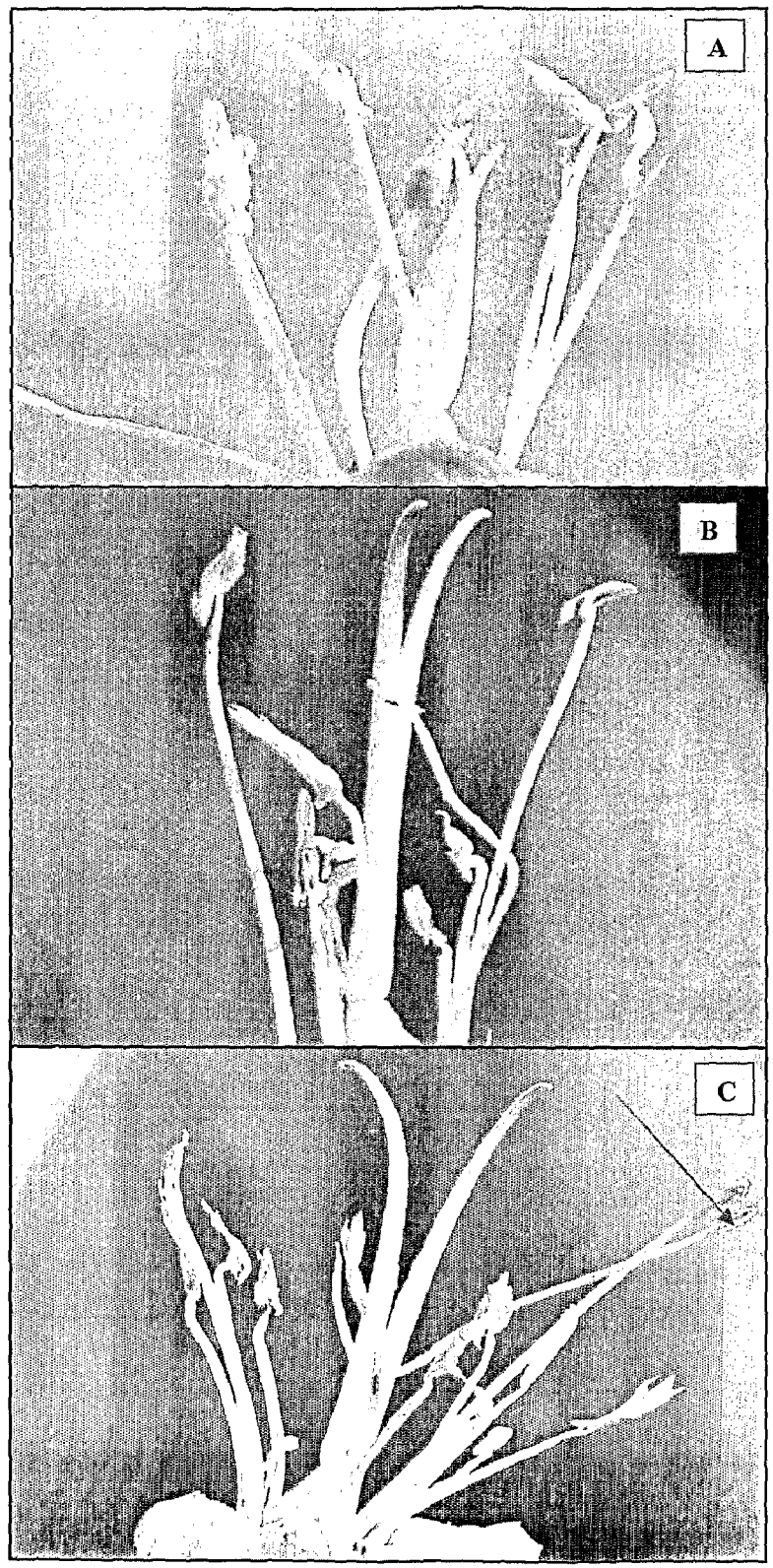
FIG. 5 is a photographic representation showing flower parts of Kortina Chanel/pCGP2442 spray carnation lines A: non-transgenic Kortina Chanel control; B: transgenic line 19907; C: transgenic line 19890. Pollen is visible (arrow).

The phenotype of two transgenic spray carnation varieties designated 19890 and 19907 were further examined. The colors of flowers from the parent line and the two transgenic lines are shown in FIGS. 3 to 5. Lines 19890 and 19907 were essentially similar to the parent in the morphological aspects of the flower (Table 7), but could be further distinguished from the parent through out the accumulation of pigment in the filaments and anthers of the flower, which was a new phenotype of the transgenic lines. Some styles and anthers of both transgenic lines also had a shift in color to light purple, whereas the styles and anthers from flowers of the parent line were a cream-white color (FIG. 5).

TABLE 7

Summary of flower measurements (mean values)

| Measurement | Parent | 19890 | 19907 |
|---|---|---|---|
| Calyx height, mm | 22 | 22 | 22 |
| Corolla height, mm | 18 | 18 | 17 |
| Flower diameter, mm | 44 | 43 | 44 |
| Petal number | 27 | 29 | 26 |
| Number of styles | 2 | 2 | 2 |
| Style length, mm | 20 | 23 | 18 |
| Number of filaments | 11 | 13 | 10 |
| Stamen length, mm | 20.3 | 23.1 | 17.6 |
| Number of anthers | 3 | 5 | 2 |
| Anther length, mm | 6.0 | 6.7 | 6.0 |
| Anther width, mm | 2.8 | 2.5 | 2.3 |
| Anther width X length, $mm^2$ | 17.3 | 16.6 | 14.1 |

Introduction of the Transformation Vector pCGP2442 into other carnation varieties Due to the success in obtaining high delphinidin levels in the carnation variety, Kortina Chanel using two chimeric F3'5'H genes and a DFR gene, the same genes are introduced into other carnation cultivars such as but not limited to Cream Cinderella, Cinderella, Cerise Westpearl, Vega, Artisan, Rendezvous.

The transgenic plants are assessed for flower color as described above and lines with novel flower color (as compared to controls) are selected for commercialization.

Introduction of Two F3'5'H Genes and a DFR Gene into Chrysanthemum.

A construct is prepared based on the expression cassettes that are functional in chrysanthemum.

An example would include the use of two F3'5'H genes such as RoseCHS:BPF3'5'H#18:nos and/or a genomic cineraria F3'5'H gene and/or carnANS 5': BPF3'5'H#18:carnANS 3' and a genomic petunia DFR gene (under the control of its own promoter and terminator) [described above].

Transformation of chrysanthemum is achieved as described_in International Patent Application No. PCT/US91/05805, U.S. Pat. No. 251,392 (US Registration No. 5,567,599) or by any other method well known in the art. For example, Aida et al, *Breeding Science*, 54:51-58, 2004; Dolgov et al, *Acta Hort* 447:329-334, 1997, Toguri et al, *Plant Biotechnology*, 20:121-127, 2003, Ledger et al, *Plant Cell Reports*, 10:195-199, 1991 or For example the transformation vector pCGP3440 contains the chimeric RoseCHS 5': BPF3'5'H#18:nos 3' gene (described in International Patent Application PCT/AU03/0111) along with a genomic cineraria F3'5'H gene (under the control of its own promoter and terminator) [SEQ ID NO:9] and a genomic petunia DFR gene (under the control of its own promoter and terminator) [SEQ ID NO:5] (described above).

The two F3'5'H genes and the DFR gene contained in the transformation vector pCGP3440, were introduced into the chrysanthemum cultivar, Improved Reagan.

A total of 52 transgenic plants were sent to soil. The plants are flowered and a selection is made on the basis of shift in color from pink to violet/purple/blue color. The delphinidin levels are measured as described above.

Introduction of Two F3'5'H Genes and a DFR Gene into Rose.

A construct is prepared based on the expression cassettes that are functional in rose. See International Patent Application No. PCT/AU03/01111 and International Patent Application PCT/JP2004/011958)

An example would include the use of two F3'5'H genes such as CaMV 35S: BPF3'5'H#18:ocs 3' and/or CaMV 35S: BPF3'5'H#40:ocs 3' and/or CaMV 35S: SalviaF3'5'H#47:ocs 3' (as described in International Patent Application No. PCT/AU03/01111) and a DFR functional in rose such as CaMV 35S: iris DFR:ocs 3' (as described in International Patent Application PCT/JP2004/011958).

Transformation of rose is achieved as described in International Patent Application PCT/JP2004/011958 or International Patent Application No. PCT/US91/04412 or Robinson and Firoozabady (*Scientia Horticulturae*, 55:83-99, 1993), Rout et al, (*Scientia Horticulturae*, 81:201-238, 1999) or Marchant et al, (*Molecular Breeding* 4:187-194, 1998) or by any other method well known in the art.

Introduction of Two F3'5'H Genes and a DFR Gene into Other Floral Crops.

pCGP2442 or its functional equivalent is used to generate genetically modified plants with altered inflorescence. Plants selected include other carnation lines such as Kortina, Royal Red Kortina, Cerise Kortina and Dusty Kortina. Non-carnation plants include chrysanthemum, rose, gerbera and other ornamental or horticultural plants such as but not limited to lisianthus, lily, geranium, *Torenia, Begonia, Cyclamen, Nierembergia, Catharanthus, Pelargonium*, orchid, grape, apple, *Euphorbia* or *Fuchsia*.

Methods used to transform and regenerate plants are as described herein or in *Scientia Horticulturae*: Transformation of Horticultural Crops, 55 (eds, Germing and Reid) Elsevier, Amsterdam, 1993, Deroles et al, In *Biotechnology of Ornamental Plants* (eds, Geneve, Preece and Markle), CAB International, Wallingford, 87-119, 1997, Tanaka et al, 2005, supra. Progeny of the genetically modified plants are capable of expressing at least two F3'5'H enzymes and at least one DFR. Color changes include a red-purple, purple, purple-violet, violet, violet-blue and blue (according to RHS color charts). Flowers may be severed from the plant and packaged for sale.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Aida et al, *Breeding Science*, 54:51-58, 2004
Altschul et al, *J. Mol. Biol.* 215 (3):403-410, 1990
Barker et al, *Plant Mol. Biol.* 2:235-350, 1983
Beld et al, *Plant Mol. Biol.* 13:491-502, 1989
Bonner and Laskey, *Eur. J. Biochem.* 46:83, 1974
Brouillard and Dangles, In: *The Flavonoids—Advances in Research since 1986*, Harborne, (ed), Chapman and Hall, London, UK, 1-22, 1993
Brugliera et al, *Plant J.* 5:81-92, 1994
Bullock et al, *Biotechniques* 5:376, 1987
da Silva, *Biotechnology Advances* 21:715-766, 2003.
Depicker et al, *J. Mol. and Appl. Genetics* 1:561-573, 1982
Deroles et al, In *Biotechnology of Ornamental Plants* (eds Geneve, Preece and Markle), CAB International, Wallingford, 87-119, 1997
Dolgov et al, *Acta Hort* 447:329-334, 1997
Forkmann and Ruhnau, *Naturforsch C.* 42c, 1146-1148, 1987
Garfinkel et al, *Cell* 27:143-153, 1983
Glimn-Lacy and Kaufman, Botany Illustrated, Introduction to Plants, Major Groups, Flowering Plant Families, 2$^{nd}$ ed, Springer, USA, 2006
Greve, *J. Mol. Appl. Genet.* 1:499-511, 1983
Holton, Isolation and characterization of petal-specific genes from *Petunia hybrida*. PhD Thesis, University of Melbourne, 1992
Holton et al, *Nature*, 366:276-279, 1993
Holton and Cornish, *Plant Cell* 7:1071-1083, 1995
Huang and Miller, *Adv. Appl. Math.* 12:373-381, 1991
Johnson et al *Plant Journal*, 19:81-85, 1999
Lazo et al, *Bio/technology* 9:963-967, 1991
Ledger et al, *Plant Cell Reports*, 10:195-199, 1991
Lu et al, *Bio/Technology* 9:864-868, 1991
Marchant et al, *Molecular Breeding* 4:187-194, 1998
Marmur and Doty, *J. Mol. Biol.* 5:109, 1962
Mol et al, *Trends Plant Sci.* 3:212-217, 1998
Pearson and Lipman, *Proc. Natl. Acad. Sci. USA* 85(8):2444-2448, 1988
Plant Molecular Biology Labfax, Croy (ed), Bios scientific Publishers, Oxford, UK, 1993 *Plant Molecular Biology Manual* (2$^{nd}$ edition), Gelvin and Schilperoot (eds), Kluwer Academic Publisher, The Netherlands, 1994
Robinson and Firoozabady, *Scientia Horticulturae*, 55:83-99, 1993
Rout et al. *Scientia Horticulturae*, 81:201-238, 1999
Salomon et al, *EMBO*, 1 3:141-146, 1984
Sambrook et al, *Molecular Cloning: A Laboratory Manual*, Cold Spring Harbor Laboratories, Cold Spring Harbor, N.Y., USA, 1989
Sambrook and Russell, *Molecular Cloning: A Laboratory Manual* 3$^{rd}$ edition, Cold Spring Harbor Laboratories, Cold Spring Harbor, N.Y., USA, 2001
Schwinn et al, *Phytochemistry*, 35:145-150, 1993
*Scientia Horticulturae*: Transformation of Horticultural Crops, 55 Germing and Reid (eds) Elsevier, Amsterdam, 1993
Seitz and Hinderer, Anthocyanins. In: *Cell Culture and Somatic Cell Genetics of Plants*. Constabel and Vasil (eds.), Academic Press, New York, USA, 5:49-76, 1988
Strack and Wray, In: *The Flavonoids—Advances in Research since 1986*. Harborne, J. B. (ed), Chapman and Hall, London, UK, 1-22, 1993
Tanaka and Mason, In *Plant Genetic Engineering*, Singh and Jaiwal (eds) SciTech Publishing Llc., USA, 1:361-385, 2003,
Tanaka et al, *Plant Cell, Tissue and Organ Culture* 80:1-24, 2005
Tanaka and Brugliera, *In Flowering and Its Manipulation, Annual Plant Reviews* Ainsworth (ed), Blackwell Publishing, UK, 20:201-239, 2006)
Thompson et al, *Nucleic Acids Research* 22:4673-4680, 1994
Toguri et al, *Plant Biotechnology*, 20:121-127, 2003
Winkel-Shirley, *Plant Physiol.* 126:485-493, 2001a
Winkel-Shirley, *Plant Physiol.* 127:1399-1404, 2001b

What is claimed is:

1. A genetically modified carnation exhibiting an altered inflorescence, wherein said carnation is genetically modified so as to express a genetic material encoding at least two flavonoid 3',5' hydroxylase (F3'5'H) enzymes encoded by SEQ ID NOs:1 and 3, respectively, and at least one dihydroflavonol-4-reductase (DFR) enzyme encoded by SEQ ID NO:5.

2. The genetically modified carnation of claim 1 wherein the altered inflorescence is in a flower, petal, anther or style of said genetically modified carnation plant.

3. The genetically modified carnation of claim 1 wherein the carnation, prior to genetic modification, is in the spray carnation *Dianthus caryophyllus* cv. Kortina Chanel or a sport thereof.

4. The genetically modified carnation of claim 3 wherein the sport is selected from the group consisting of Kortina, Royal Red Kortina, Cerise Kortina and Dusty Kortina.

5. The genetically modified carnation of claim 1 wherein the carnation, prior to genetic modification, is Cerise Westpearl, Vega, Artisan, Cream Cinderella, Cinderella or Rendezvous.

6. The genetically modified carnation of claim 1 wherein the carnation is Kortina Chanel/2442.

7. Progeny, reproductive material, cut flowers, tissue culturable cells or regenerable cells from the genetically modified carnation of claim 1, wherein said progeny, reproductive material, cut flowers, tissue culturable cells or regenerable cells are genetically modified so as to express a genetic material encoding at least two flavonoid 3',5' hydroxylase (F3'5'H) enzymes encoded by SEQ ID NOs:1 and 3, respectively, and at least one dihydroflavonol-4-reductase (DFR) enzyme encoded by SEQ ID NO:5.

8. A method for producing a carnation exhibiting an altered inflorescence as a result of genetic modification, said method comprising:
   introducing into regenerable cells of a carnation plant an expressible genetic material encoding at least two F3'5'H enzymes encoded by SEQ ID NOs:1 and 3, respectively, and at least one DFR enzyme encoded by SEQ ID NO:5, and
   regenerating a plant therefrom which comprises said at least two F3'5'H enzymes and said at least one DFR enzyme, and optionally, obtaining progeny of the regenerated plant, which progeny comprise said at least two F3'5'H enzymes and said at least one DFR enzyme.

9. A method for producing a carnation line exhibiting altered inflorescence as a result of genetic modification, the method comprising:
   selecting a spray carnation plant comprising a genetic material encoding one of at least two F'3'5'H enzymes encoded by SEQ ID NOs:1 and 3, respectively, and at least one DFR enzyme encoded by SEQ ID NO:5;
   crossing this plant with another carnation comprising a genetic material encoding the other of at least two F3'5'H enzymes encoded by SEQ ID NOs:1 and 3, respectively, and at least one DFR enzyme encoded by SEQ ID NO:5, and then
   selecting F1 or subsequent generation plants, which F1 or subsequent generation plants comprise said at least two F3'5'H enzymes and said at least one DFR enzyme.

* * * * *